US006436058B1

(12) United States Patent
Krahner et al.

(10) Patent No.: US 6,436,058 B1
(45) Date of Patent: Aug. 20, 2002

(54) SYSTEM AND METHOD FOR IMPLEMENTING REHABILITATION PROTOCOLS FOR AN ORTHOPEDIC RESTRAINING DEVICE

(75) Inventors: Angela M. Krahner, San Diego; Daniel S. Pflaster, Carlsbad; Charles A. Bastyr, Del Mar; Marjorie Ann Rowland, Vista, all of CA (US)

(73) Assignee: DJ Orthopedics, LLC, Vista, CA (US)

( * ) Notice: Subject to any disclaimer, the term of this patent is extended or adjusted under 35 U.S.C. 154(b) by 7 days.

(21) Appl. No.: 09/594,426

(22) Filed: Jun. 15, 2000

(51) Int. Cl.$^7$ ................................ A61G 5/103
(52) U.S. Cl. .......................... 600/587; 482/1
(58) Field of Search ................. 600/587–595; 482/1–9, 51–78, 84–90

(56) References Cited

U.S. PATENT DOCUMENTS

| | | | |
|---|---|---|---|
| 4,801,138 A | 1/1989 | Airy et al. | |
| 5,052,375 A | 10/1991 | Stark et al. | |
| 5,052,379 A | 10/1991 | Airy et al. | |
| 5,368,546 A | 11/1994 | Stark et al. | |
| 5,410,472 A | * 4/1995 | Anderson | 482/9 |
| 5,474,088 A | 12/1995 | Zaharkin et al. | |
| 5,484,389 A | 1/1996 | Stark et al. | |
| 5,823,975 A | 10/1998 | Stark et al. | |
| 5,921,946 A | 7/1999 | Tillinghast et al. | |
| 5,929,782 A | 7/1999 | Stark et al. | |
| D420,650 S | 2/2000 | Feirbach | |
| D424,534 S | 5/2000 | Priestman et al. | |
| D425,558 S | 5/2000 | Tarpenning et al. | |

FOREIGN PATENT DOCUMENTS

WO  WO 9636278  11/1996
WO  WO 9846441  10/1998

OTHER PUBLICATIONS

Body Trends Online, "Resistive Exercise Systems," http://www.bodytrends.com/ncm.htm, 2 pages, downloaded and printed from the World Wide Web on or about Mar. 24, 2000.
Photograph No. 1 of a monitoring device having a monitor and a brace, designed by IZEX Technologies, Inc. and introduced to Applicants on or around Aug. 23, 1996.
Photograph No. 2 of a monitor for a monitoring device by IZEX Technologies, Inc. and introduced to Applicants on or around Aug. 23, 1996.
Photograph No. 3 of a brace for a monitoring device by IZEX Technologies, Inc. and introduced to Applicants on or around Aug. 23, 1996.
Photograph No. 4 of a brace for a monitoring device by IZEX Technologies, Inc. and introduced to Applicants on or around Aug. 23, 1996.
Photograph No. 5 of an output screen for a monitoring device by IZEX Technologies, Inc. and introduced to Applicants on or around Aug. 23, 1996.

(List continued on next page.)

*Primary Examiner*—Kevin Shaver
*Assistant Examiner*—Pamela Wingood
(74) *Attorney, Agent, or Firm*—Knobbe, Martens, Olson and Bear, LLP.

(57) ABSTRACT

The invention comprises a system and method for implementing a rehabilitation protocol in a monitoring system for an orthopedic restraining device. The monitoring system provides clinician-recommended parameters for a wide number of exercises in the rehabilitation protocol, instructs a patient on how to perform the exercises, stores data relating to the patient's performance, and presents data to a clinician for analysis of the data. The orthopedic restraining device includes visual indicia while a monitoring device includes demonstration and review protocol modes.

22 Claims, 17 Drawing Sheets

OTHER PUBLICATIONS

Photograph No. 6 of an output screen for a monitoring device by IZEX Technologies, Inc. and introduced to Applicants on or around Aug. 23, 1996.
Photograph No. 7 of an output screen for a monitoring device by IZEX Technologies, Inc. and introduced to Applicants on or around Aug. 23, 1996.
Photograph No. 8 of an output screen for a monitoring device by IZEX Technologies, Inc. and introduced to Applicants on or around Aug. 23, 1996.
Photograph No. 9 of an output screen for a monitoring device by IZEX Technologies, Inc. and introduced to Applicants on or around Aug. 23, 1996.
Photograph No. 10 of an output screen for a monitoring device by IZEX Technologies, Inc. and introduced to Applicants on or around Aug. 23, 1996.
Photograph No. 11 of an output screen for a monitoring device by IZEX Technologies, Inc. and introduced to Applicants on or around Aug. 23, 1996.
Description of Software Code for a monitoring device by IZEX Technologies, Inc., the Software Code being introduced to Applicants on or around Nov. 5, 1998, 3 pages, titled, "IZEX Rehab Prototype."
U.S. patent application Ser. No. 08/388,879.
U.S. patent application Ser. No. 08/520,802.
U.S. patent application Ser. No. 08/442,945.
U.S. patent application Ser. No. 08/824,065.
U.S. Provisional application No. 60/098,779.
U.S. patent application Ser. No. 09/226,866.
U.S. patent application Ser. No. 09/339,071.
U.S. patent application Ser. No. 09/330,749.
U.S. patent application Ser. No. 09/329,880.
U.S. patent application Ser. No. 09/416,192.
U.S. patent application Ser. No. 29/124,975.

* cited by examiner

| PACING EXERCISE PERFORMANCE DATA |
|---|
| exercise ID — 755 |
| incomplete / complete status — 760 |
| pain status — 765 |
| current set — 770 |
| locked angle — 775 |
| current rep — 780 |
| maximum extension angle — 785 |
| maximum flexion angle — 790 |

| PROGRESSIVE GOAL DATA |
|---|
| exercise ID |
| incomplete / complete status |
| pain status |
| current set |
| current rep |
| locked angle |
| set-up load |
| maximum peak torque |
| average peak torque |
| maximum extension angle |
| maximum flexion angle |

SYSTEM AND METHOD FOR IMPLEMENTING REHABILITATION PROTOCOLS FOR AN ORTHOPEDIC RESTRAINING DEVICE

BACKGROUND OF THE INVENTION

1. Field of the Invention

This invention relates in general to orthopedic rehabilitation devices, and in particular, to a system and method for implementing rehabilitation protocols for such devices.

2. Description of the Related Art

It is widely known that injuries to bones, muscle tissue, connective tissue, and the like, often heal faster, stronger, and more predictably with physical therapy. For a patient needing physical therapy, a clinician typically prescribes a rehabilitation protocol, or exercise regimen, specifically designed for that patient. The rehabilitation protocol often includes a wide number of differing exercises depending upon the type of injury and patient progression with rehabilitation. In addition, the rehabilitation protocol generally includes specific recommendations for each exercise. For example, each exercise may differ in its recommended number of repetitions, sets, motions, duration, resistance, frequency, and the like. In performing the rehabilitation protocol, the patient has to remember which exercises were prescribed by a clinician, how to perform those exercises, and of those exercises, which parameter recommendations were provided. Moreover, the patient has to record or remember his or her success and progression for each exercise such that the clinician can accurately analyze the patient's progress.

However, patients often provide inaccurate data regarding their performance of rehabilitation protocols. Such inaccuracies come from a wide number of possible sources. For example, a patient often does not follow a particular protocol because of pain, lack of motivation, misunderstanding, or simply forgetting some or all of the parameters and instructions associated with each exercise. For these and other reasons, the patient may keep inaccurate data for a given exercise. On the other hand, the patient may keep accurate or inaccurate data of an exercise performed improperly, or even keep no data at all. In each of the foregoing situations, a clinician may be placed in the position of modifying a rehabilitation protocol based on inaccurate patient data. By relying on inaccurate data, the clinician may exacerbate the patient's condition, and thereby potentially harm the patient's rehabilitation progress.

Therefore, a need exists to develop a system that allows clinicians to prescribe rehabilitation protocols, that motivates and instructs patients in how to follow the protocols, that tracks the patients' progress through the protocols, and that accurately reports the data back to the clinicians.

One system attempting to meet the foregoing need is disclosed in U.S. Pat. No. 5,823,975, issued to Stark et al. (the "Stark reference"). The Stark reference discloses a monitoring system for an orthopedic brace. The Stark system includes a monitoring device, clinician software, and a brace having a hinge with an incrementally adjustable lock. The brace includes an angle sensor for detecting an angle between components of the hinge. The brace also includes a load sensor for detecting a load on the brace. The angle sensor and the load sensor communicate with the monitoring device such that the monitoring device records data from the brace. The monitoring device also communicates with the clinician software such that the recorded data is uploaded to the clinician software and protocol parameters are downloaded to the monitoring device.

Using the Stark system, a clinician downloads preferably his or her recommended exercise parameters into the monitoring device. The patient views instructions relating to recommended exercises, performs the recommended exercises, and the monitoring device records data from the sensors relating to the performance. Later, the recorded data is uploaded to the clinician software for analysis by the clinician.

Thus, the Stark system provides the brace, the monitoring device, and the clinician software, which enable clinicians to prescribe and receive data regarding patient rehabilitation protocols. However, the Stark system suffers from a variety of drawbacks causing the components individually, and the Stark system as a whole, to be inefficient and cumbersome.

For example, the Stark system fails to incorporate visual indicia on the brace representing differing configurations of the brace. Rather, the Stark system relies entirely on the monitoring device to provide feedback to the patient as to the recommended lock angle for the brace. For example, when the patient is to lock the brace at a twenty-degree angle, the patient moves the brace until the monitoring device confirms the brace is configured to twenty-degrees. The patient then locks the brace at that configuration. Such reliance on the monitoring device is problematic for several reasons. On one hand, the angle sensor on the brace may be miscalibrated, thereby causing the patient following the monitoring device to exceed the prescribed range of motion. In addition, the patient must redirect the focus of their attention from the monitoring device to the brace in order to lock the brace at the correct angle. Such action again may cause the patient to set the brace at angles differing from those prescribed.

The Stark brace also fails to provide limit stops for limiting the available range of motion in the brace. Rather, the Stark brace either locks at a particular setting, or is free to move through the entire range of motion provided by the brace. Moreover, the Stark system fails to recommend resistance types or amounts, thereby forcing the clinician to prescribe portions of the rehabilitation protocol outside the system, or to simply leave such decisions to patient guesswork. Also, the Stark system fails to provide a protocol review mode, thereby limiting the clinician in their ability to quickly determine or review which of potentially many protocols is loaded on a given monitoring device.

Moreover, the Stark system includes a very limited and absolute rehabilitation protocol. For example, the Stark system includes only a few transducer-oriented exercises focusing on loads and positions. In addition, for each of those exercises, the Stark system employs absolute load and position parameters. Such absolute parameters are generally overly limiting and often counterproductive. For example, an absolute parameter generally pushes patients to reach the parameter from the very beginning. Therefore, in order to ensure safe operation, the clinician will be inclined to set very low initial exercise parameters, and then reset those parameters based on each patient's progression. Such resetting may require frequent patient visits and/or monitoring device uploads and data analysis. In addition, if the clinician wrongly estimates a patient's abilities or injury, the initial low parameters may induce the patient to become unmotivated based on early goal attainment or abysmal failure.

Also, the Stark system is inefficient in the manner it gathers and stores data, thereby requiring the monitoring device to include large and often expensive data storage capabilities. For example, the Stark system stores real-time data from the sensor at a given sample rate. Such sampled data consists of many data points. Storage of many data points dictates either large storage capacity needs on the Stark monitoring device or frequent data uploads to the clinician software. In addition, the Stark sampled data points also dictate sophisticated clinician software to map the data points to timing graphs and sophisticated clinician analysis to track patient progress. Based on the above, the Stark system stores inefficient data, some of which may not be intuitive or even analyzable to ordinary physical therapists. Such storage dictates expensive storage capacity or frequent uploads. In addition, such storage may limit the clinician's ability to delegate patient progress monitoring.

Based on the above, a need exists to provide a system for implementing rehabilitation protocols that is flexible, comprehensive, and efficient.

SUMMARY OF THE INVENTION

Therefore, one aspect of the present invention is to provide a system for implementing rehabilitation protocols that is flexible, comprehensive, and efficient. In addition, the monitoring system allows clinicians to fully prescribe rehabilitation protocols, motivates and instructs patients in how to follow the protocols, tracks the patients' progress through the protocols, and accurately and efficiently reports the data back to the clinicians. According to another aspect of the invention, the system includes integration of resistance recommendations and visible indicia representing brace configurations and position limits into the system firmware. According to another aspect of the invention, the system includes progressive goal setting combined with a phase implementation of the rehabilitation protocol, and efficient data storage.

Accordingly, one aspect of the invention includes a method of monitoring and displaying patient progress with a rehabilitation protocol. The method comprises automatically measuring at least one parameter of an orthopedic brace used during repetitions of at least one rehabilitation exercise and displaying a first indicator representative of a current value of the at least one parameter corresponding to a current repetition. The method also includes displaying a second indicator representative of a previous maximum attained value of the at least one parameter corresponding to a previous repetition, wherein said first and second indicators are displayed comparatively.

According to another aspect, the invention includes a monitoring device for monitoring and displaying selected characteristics of an orthopedic brace used for the performance of at least one rehabilitation exercise. The monitoring device comprises circuitry adapted to receive data from an orthopedic brace, the data representing one or more values of at least one characteristic of the orthopedic brace. The device also includes a memory configured to store the data where the data includes a current value of the at least one characteristic and a previous value of the at least one characteristic. The device also has a microcontroller programmed to output to a display the current value and the previous value such that an operator's comparison of the current value and the previous value motivates the operator to increase his or her performance of at least one exercise.

According to yet another aspect, the invention includes a method of dynamically normalizing a performance recommendation of a rehabilitation protocol stored in a monitoring device for monitoring at least one parameter of an orthopedic brace used during an exercise. The method comprises indicating a performance recommendation to a patient for a parameter of an exercise of a rehabilitation protocol, wherein the performance recommendation is a percentage of a predetermined amount of effort. The method also comprises sensing a value of the parameter from an orthopedic brace during a first performance of the exercise and displaying an indicator corresponding to the value of the parameter as a goal during at least one subsequent performance of the exercise.

According to another aspect, the invention includes a monitoring device for monitoring performance parameters of an exercise routine to determine an operator's compliance with the exercise routine. The monitoring device comprises a memory configured to store recommendations for performance parameters of an exercise routine. The device also includes a microcontroller programmed to dynamically normalize at least one recommendation of at least one exercise of the exercise routine to a particular operator through an effort calibration, to use a result of the effort calibration as a goal, and to output a display signal representative of the goal to a display such that the operator attempts to reach the goal during a performance of the at least one exercise.

According to yet another aspect, the invention includes a monitoring device for monitoring selected parameters of an orthopedic brace during an exercise routine, the orthopedic brace having a plurality of configurations and visible indicia uniquely identifying at least one of the plurality of configurations of the orthopedic brace. The monitoring device comprises a memory configured to store data representing at least one configuration of an orthopedic brace for at least one exercise of an exercise routine, wherein a portion of the data represents values of visual indicia on the orthopedic brace corresponding to the at least one configuration. The monitoring device also comprises a microcontroller programmed to read the data from the memory and output to a display at least the portion of the data representing the values of the visual indicia corresponding to the at least one configuration such that an operator, in preparation of performing the at least one exercise, can set the orthopedic brace to the at least one configuration by using the visual indicia on the orthopedic brace.

According to another aspect, the invention includes a method of electronically monitoring parameters of an orthopedic brace during performance of an isometric exercise. The method comprises monitoring a torque placed on an orthopedic brace during the performance of an exercise, and storing the repetition as a successful repetition when a characteristic of the torque matches a predetermined value.

According to yet another aspect, the invention includes a method of monitoring a performance of an exercise with an electronic device. The method comprises storing data relating to a performance of at least one exercise in a memory of an electronic device, wherein the data does not include information from a torque or range of motion transducer.

BRIEF DESCRIPTION OF THE DRAWINGS

The present invention is described in more detail below in connection with the attached drawings, which are meant to illustrate and not limit the invention, and in which.

DETAILED DESCRIPTION OF THE PREFERRED EMBODIMENT

The present invention includes a monitoring system for implementing a rehabilitation protocol having progressive and dynamic goals, an expanded exercise protocol, and efficient data storage. In addition, the monitoring system advantageously incorporates visual indicia from a rehabilitation device into the rehabilitation protocol such that patients may efficiently and properly configure the rehabilitation device during execution of the protocol. In order to facilitate a complete understanding of the invention, the remainder of this detailed description describes the invention with reference to the figures, wherein like elements are referenced with like numerals throughout.

Figure 1:
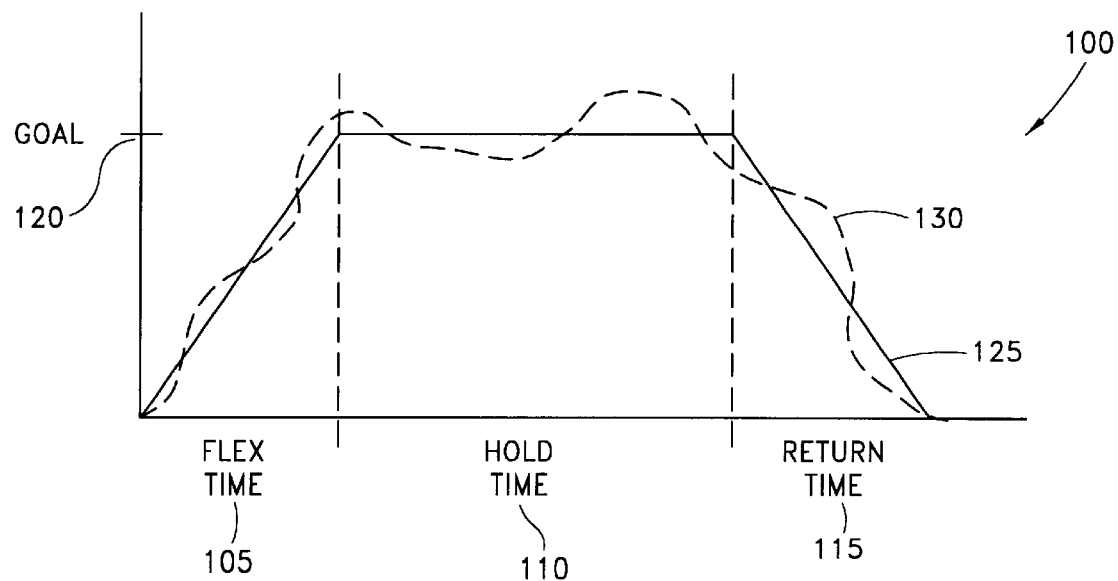
FIG. 1 illustrates the content of an exemplary exercise screen in accordance with the prior art.

FIG. 1 illustrates the content of an exemplary isometric exercise screen in accordance with the prior art. As shown in FIG. 1, the display includes a graph 100 divided along its horizontal axis into three sections, a flex time 105, a hold time 110, and a return time 115, all in seconds. The vertical axis of the graph 100 includes the torque goal 120, in ft-lbs. The solid line 125 is created from the clinician-input parameters, such as, for example, the clinician input the flex time 105, the hold time 110, the return time 115, and the goal 120. As the patient applies a torque to the brace, a broken or cursor line 130 reflects the actual torque. According to the prior art, the patient should attempt to match the cursor line 130, or actual torque, to the solid line 125, or torque goal. As shown in FIG. 1, assuming that a patient can even apply a great enough torque to the brace to reach the absolute goal 120, the patient at best will be oscillating around the solid line 125. Such oscillation will mean that the patient is over and under exerting. Again, such over and under performance of the Stark protocol may potentially lead to pain and further injury.

In addition, the clinical benefits of trying to follow a given exercise curve are suspect. In fact, the curve represented by the solid line 125 may even be counterproductive. For example, even healthy patients may have difficulty applying just enough torque to follow the solid line 125, and the failure to do so often leads to negative psychological reinforcement for the patient about his or her personal progress.

Also, the exemplary isometric exercise screen of FIG. 1 does not represent typical clinician instructions. For example, clinicians often can not give an absolute torque goal in ft-lbs for each patient because they are unfamiliar with absolute units of torque and the magnitude thereof will differ from patient to patient. Thus, the clinician may over generalize the torque recommendation or be faced with learning differing absolute torque goals that correspond to differing patient conditions and abilities.

THE MONITORING SYSTEM

Figure 2A:
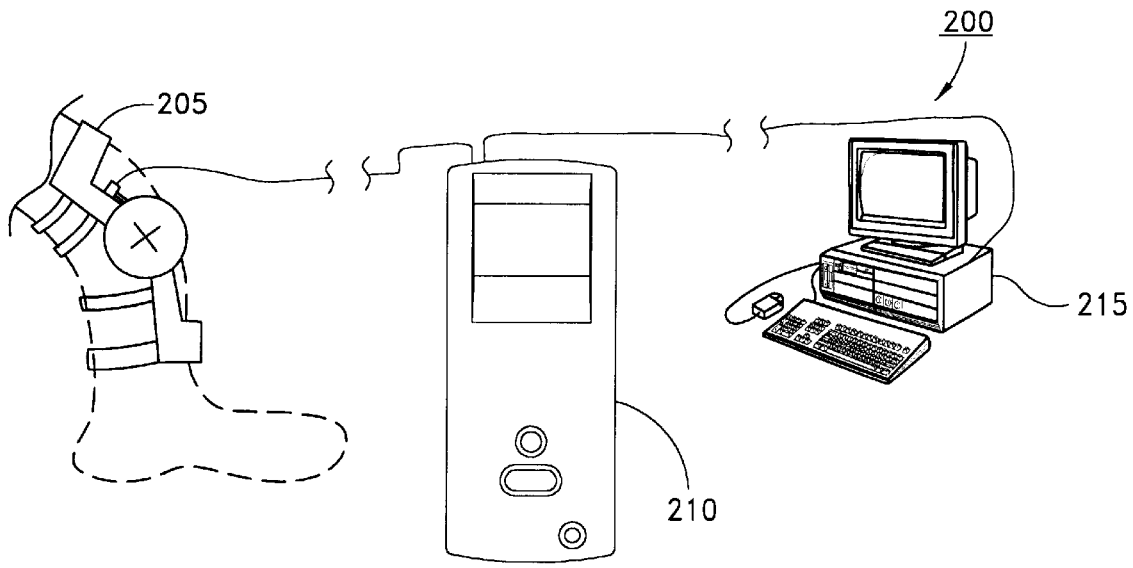
FIG. 2A illustrates a simplified perspective view of a monitoring system having features according to aspects of an embodiment of the invention.

FIG. 2A illustrates a simplified perspective view of a monitoring system 200 having features according to an embodiment of the invention. As shown in FIG. 2A, the monitoring system 200 includes a brace hinge assembly 205, a monitoring device 210, and a clinician system 215. The brace hinge assembly 205 preferably communicates with the monitoring device 210 such that the monitoring device 210 records performance data from the brace 205. From time to time, the monitoring device 210 preferably communicates with the clinician system 215 so as to download rehabilitation protocols, upload stored performance data, and, if desired, download updates to the computer program (firmware) executing within the monitoring device 210.

Figure 2B:
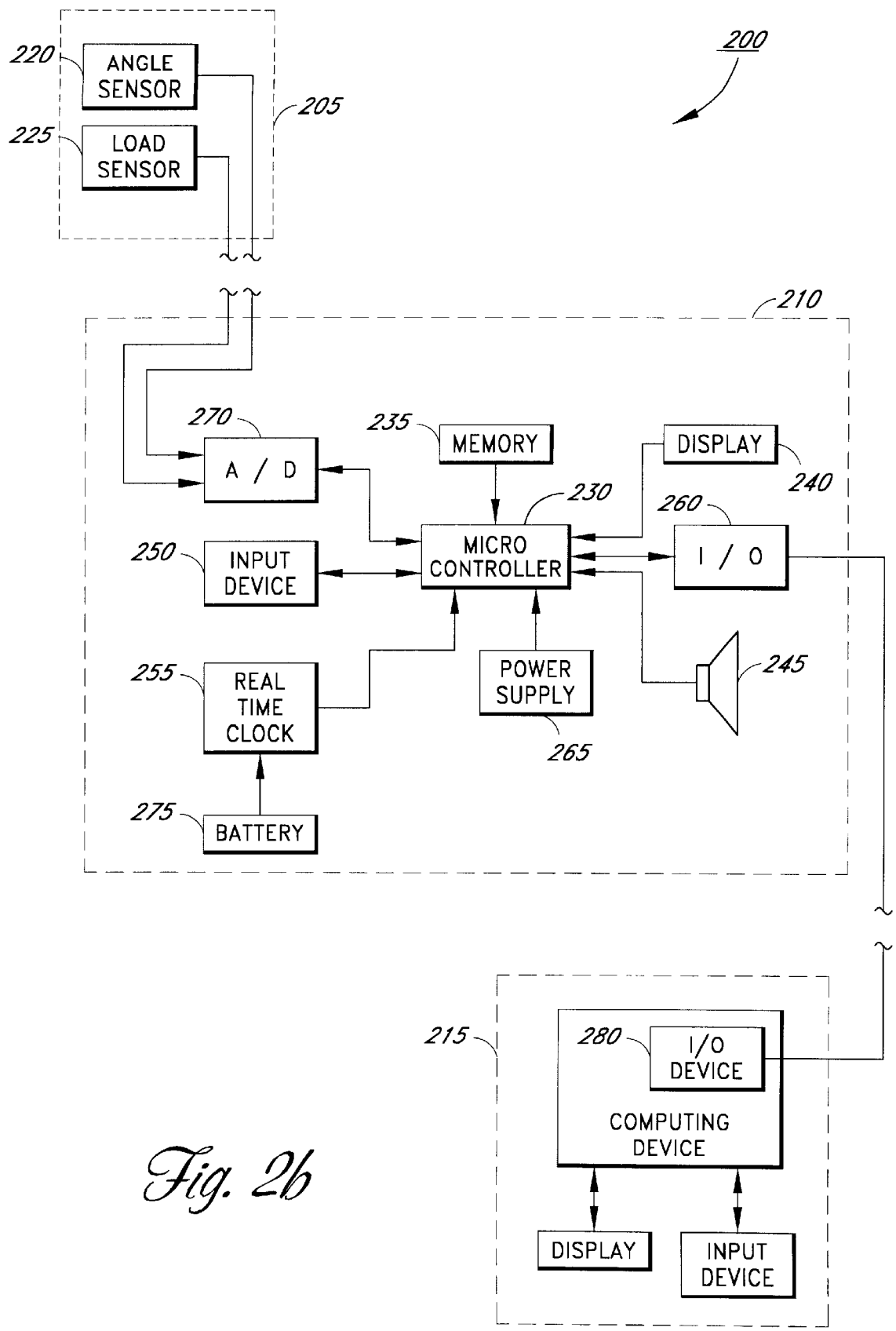
FIG. 2B illustrates a block diagram of the monitoring system of FIG. 2A.

FIG. 2B illustrates a block diagram of the monitoring system 200 of FIG. 2A. As shown in FIG. 2B, the monitoring system 200 preferably includes the brace hinge assembly 205, the monitoring device 210, and the clinician system 215. The brace hinge assembly 205 comprises an angle sensor 220 and a load sensor 225. Preferably, the angle sensor 220 comprises a rotational sensor positioned within the brace hinge assembly 205. The rotational sensor may advantageously be a potentiometer, as described in the Stark reference, or more preferably, a Hall effect senor, as described in U.S. patent application Ser. No. \*\*/\*\*\*,\*\*\*, filed on Apr. 26, 2000, titled "Angle Sensor For Orthopedic Rehabilitation Sevice," assigned to the instant assignee, and incorporated by reference herein. The load sensor 225 preferably comprises a strain gage, such as a conventional resistive strain gage.

The monitoring device 210 includes a microcontroller 230 connected to a memory 235, a display 240, an audio/vibrational output 245, a patient input device 250, a real time clock (RTC) 255, a clinician communicator 260, a power supply 265, and a brace communicator 270. The microcontroller 230 preferably includes a microcontroller capable of executing program instructions and preferably capable of communicating with the foregoing components of the monitoring device 210. According to the preferred embodiment, the microcontroller 230 includes a Motorola 68HC11K1 8-bit microcontroller with an integrated 8-channel 8-bit analog-to-digital converter, real-time interrupt circuit, and six expandable address lines. The monitoring device 210 preferably includes firmware. Firmware is generally defined as software or computer instructions stored in a non-volatile memory such that powering off the monitoring device 210 does not affect the storage of the software.

According to the preferred embodiment, the memory 235 preferably comprises non-volatile memory for storing the firmware, the rehabilitation protocol, and performance data. Most preferably, the memory 235 comprises two peripheral 128 k non-volatile flash memory chips, one for preferably storing the firmware and the other for preferably storing the rehabilitation protocol and performance data. According to another embodiment, the memory 235 may also advantageously comprise a peripheral 32 k SRAM chip that is preferably battery backed.

The display 240 comprises a display screen for showing text and graphics relating to the firmware, the rehabilitation protocol, and the performance data. According to the preferred embodiment, the display 240 comprises a 128×64 LCD graphic module. However, a skilled artisan would recognize a wide number of conventional devices, from the disclosure herein, that may connect to the monitoring device 210 and display the foregoing text and graphics. For example, the display 240 may advantageously comprise a color monitor, a conventional or digital television, a personal digital assistant, or the like.

The audio/vibrational output 245 preferably provides notification of events to the user of the monitoring system 200. According to the preferred embodiment, the audio/vibrational output 245 comprises a beeper. However, a skilled artisan will recognize from the disclosure herein that the audio/vibrational output 245 may advantageously include an audio transducer or other conventional means. Moreover, the audio/vibrational output 245 may connect to a home stereo system, an alarm clock, or other conventional household electronic device.

The patient input device 250 preferably allows the patient to interact with the monitoring device 210. According to the preferred embodiment, the patient input device 250 comprises two keys for operator input. However, a skilled artisan would recognize from the disclosure herein that a wide number of patient input mechanisms may be used for the patient input device 250. For example, the patient input device 250 may advantageously comprise a pointing device, a keyboard, a touch screen, a vocal comprehension device, or the like.

The RTC 255 preferably comprises a battery backed real time clock for time stamps, wake-up capability, and automatic powering-off of the system. A backup battery 275 preferably has a minimum life of three years, such as 3V lithium battery to back-up the RTC 255.

The clinician communicator 260 preferably provides communication of data to the clinician system 215. Such communication advantageously includes downloading rehabilitation protocols, uploading patient data, and upgrading the firmware. According to the preferred embodiment, the clinician communicator 260 comprises an RS232 transceiver.

The power supply 265 preferably provides sufficient power for the monitoring device 210 to operate. Preferably, the main power supply comprises standard replaceable or rechargeable batteries, such as two 'AA' batteries. However, a skilled artisan will recognize from the disclosure herein that the power supply 265 may advantageously include conventional outlet technology, or other conventional power supply systems.

The brace communicator 270 preferably receives data from the brace hinge assembly 205. Such data advantageously includes communication with the angle sensor 220 and the load sensor 225. According to one embodiment of the invention, the brace communicator 270 comprises an analog-to-digital converter and the data received from the brace hinge assembly 205 comprises analog signals. The brace communicator 270 receives the analog signals, and converts the analog signals into digital data. The brace communicator 270 preferably transfers the digital data to the microcontroller 230. The microcontroller 230 reads the digital data and preferably transforms the digital data into respective angle and load or torque values. According to the preferred embodiment, the angle values represent whole integers of one-degree resolution while the load or torque values represent whole integers of one Newton-meter (Nm) resolution.

The clinician system 215 preferably includes a personal computer such as those commercially available. The clinician system 215 also includes a monitoring device communicator 280. The monitoring device communicator 280 is configured to communicate with the clinician communicator 260. For example, the preferred monitoring device communicator 280 advantageously comprises an RS232 transceiver.

Although the monitoring system 200 is disclosed with reference to its preferred embodiment, the invention is not intended to be limited thereby. Rather, an artisan skilled in transducers or computer system design and programming will recognize from the disclosure herein a wide number of alternatives embodiments for the components of the brace hinge assembly 205, the monitoring device 210, and the clinician system 215. For example, the communication between the brace hinge assembly 205 and the monitoring device 210, or between the monitoring device 210 and the clinician system 215, may advantageously comprise a wide number of data transfer methodologies. For example, the data may advantageously be transferred by one or a combination of the following communication systems: telephonic systems and signals, radio frequency signals, internet systems, wide or local area networks, personal digital assistants, cellular phones/technology, infrared signals, satellite communications, mass storage transfer and the like. In addition, the monitoring device 210 may comprise a personal computer, computer system, laptop, personal digital assistant, wireless devices, such as, for example, cellular phones, handheld computing device, or the like. Moreover, the monitoring device 210 may include printer connections such that the patient or clinician can print reports relating to system integrity, patient data, program data, rehabilitation protocol data, or the like.

Figure 3:
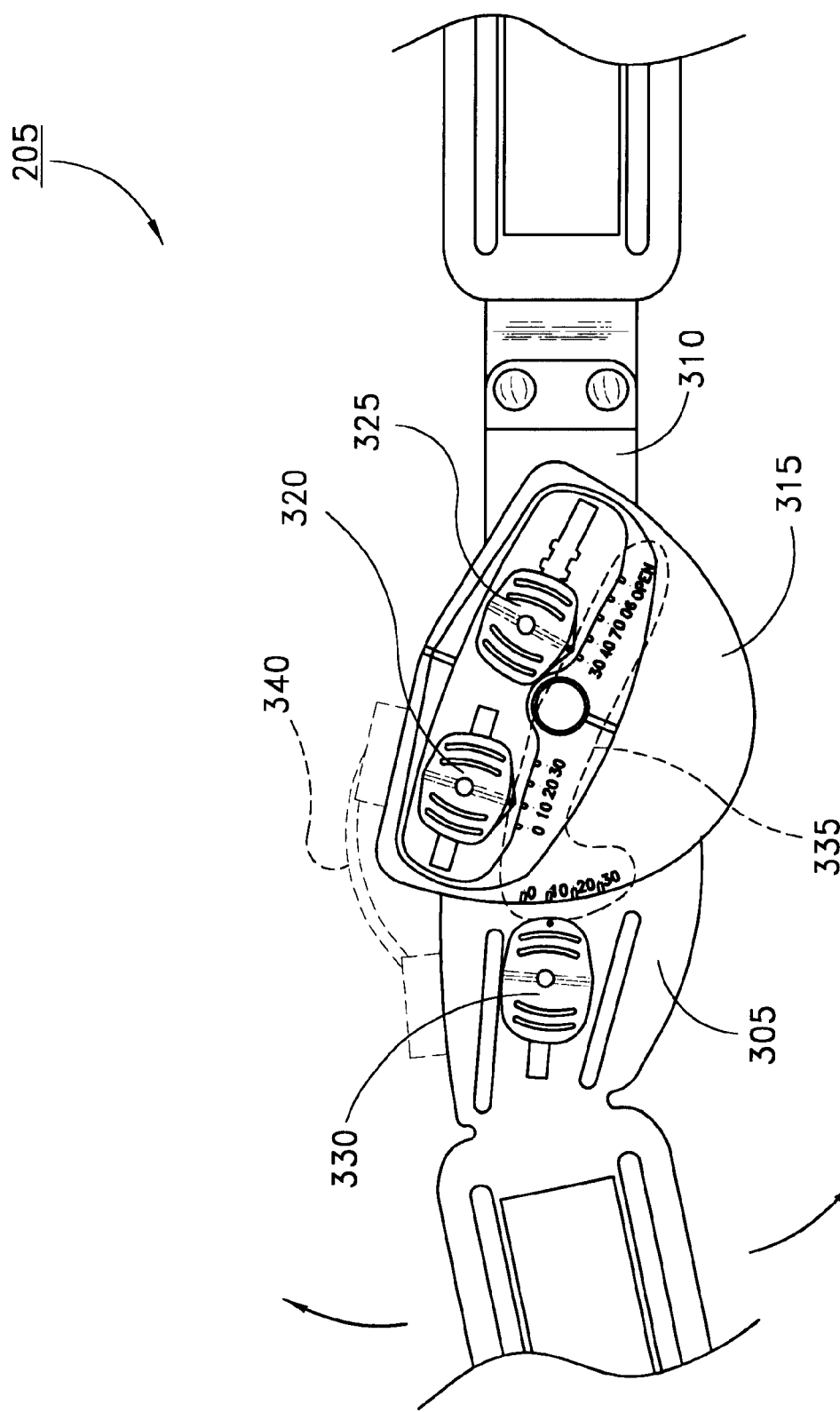
FIG. 3 illustrates a simplified side view of an exemplary brace hinge assembly, according to the monitoring system of FIGS. 2A and 2B.

FIG. 3 illustrates a simplified side view of the brace hinge assembly 205. According to the preferred embodiment, the brace hinge assembly 205 comprises an orthopedic knee brace. However, one of ordinary skill in the art will understand that the brace hinge assembly 205 may comprise a variety of suitable devices. As shown in FIG. 3, the brace hinge assembly 205 comprises a first bar 305 and a second bar 310. The first bar 305 is pivotally coupled to the second bar 310 by a hinge (not shown) such that the first bar 305 pivots in the directions indicated in FIG. 3. The hinge and portions of the first bar 305 and the second bar 310 are covered by a face plate 315. Further disclosure of the brace hinge assembly 205 can be found in U.S. Pat. No. 5,921,946, issued on Jul. 13, 1999, titled *"Joint Brace Hinges,"* assigned to the instant assignee, and incorporated by reference herein.

The face plate 315 includes an extension limiter 320, a flexion limiter 325, and an angle lock 330. The extension limiter 320 and the flexion limiter 325 advantageously limit the angular range available to the hinge. For example, the extension limiter 320 may be set at ten degrees and the flexion limiter 325 at forty degrees. With such settings, the brace hinge assembly 205 now limits the range of motion for the first bar to any angle between ten and forty degrees. The angle lock 330 locks the hinge at a specified angle. For example, the angle lock 330 may advantageously be set to twenty degrees. At such configuration, the brace hinge assembly 205 cannot move from the set twenty degree angle.

The face plate 315 also comprises visible indicia 335. The visible indicia 335 advantageously provide indications to the patient, not only of the available settings for the extension limiter 320, flexion limiter 325, and the angle lock 330, but also whether any of the foregoing is set. For example, the preferred visual indicia include the following: indicia indicating extension; indicia indicating extension stops at angles 0°, 10°, 20°, and 30°; indicia indicating flexion; indicia indicating flexion stops at angles 30°, 40°, 70°, 90°, and Open; indicia indicating locks; and indicia indicating locks at angles 0°, 10°, 20°, 30°, 40°, 50°, 60°, 70°, 80°, and 90°. However, a skilled art may recognize from the disclosure herein, other visual indicia that provide for efficient, accurate, and safe application and use of the brace hinge assembly 205. According to the preferred embodiment, the values of the visual indicia 335 are advantageously programmed such that the monitoring device 210 instructs patients on the recommended parameters corresponding to the visual indicia 335.

FIG. 3 also shows the brace hinge assembly 205 optionally including a resistance applicator 340 (shown in phantom). The resistance applicator 340 may advantageously comprise two connectors, each removably attached to one of the first bar 305 and an interior plate of the hinge. A flexible material or band advantageously attaches the connectors to each other. The flexible material or band preferably provides a resistance to a patient trying to bend the brace hinge assembly 205. The resistance applicator 340 may advantageously be color coded such that different colors correspond to known differing resistance forces, based, for example, on the thickness or composition of the flexible material. According to the preferred embodiment, the color-coding is advantageously programmed into the firmware such that the monitoring device 210 instructs patients on the recommended color of the resistance applicator 340. In addition to recommending the resistance to the patient, the monitoring device 210 may advantageously employ the load sensor 225 during monitoring to measure the patient's compliance with the recommended resistance values. The load compliance values may advantageously be stored in the memory 235 along with other performance data.

In addition to the foregoing resistance applicator 340 applying a flexion resistance, the brace hinge assembly 205 may include a similar resistance mechanism for applying an extension resistance. According to this embodiment, the extension resistance mechanism employs connectors on the opposite side of the first bar 305 and the interior plate of the hinge. A similar flexible material or band preferably connects the connectors, thereby providing resistance to the patient trying to extend or straighten the brace hinge assembly 205.

One of ordinary skill in the art will recognize from the disclosure herein that the flexible material for either the flexion or extension resistance may removably attach to the fixed connectors on the first bar 305 and the interior plate of the hinge such that the material, as opposed to the connectors and material, are replaced. Moreover, the flexible material may advantageously comprise a spring, Theraband structure, or the like. The flexible material may include nonflexible components. For example, the mechanism actually supplying the resistance may be incorporated into, or moved toward, the ends or center of the resistance applicator 340. In addition, the connectors may attach to the second bar 310 or the face plate 315.

According to another embodiment, as a supplement to, or a replacement of, the resistance applicator 340, the firmware may also advantageously include the ability to store clinician recommendations of other more conventional resistance devices. For example, the firmware may store recommendations for an amount of weight, a color of Theraband, or other known types and parameters of conventional resistance devices.

THE FIRMWARE

According to the preferred embodiment, the rehabilitation protocol is broken into phases, days, sessions, exercises, sets and repetitions ("reps"). Each phase preferably comprises a number of days, and each day preferably comprises a number of sessions, each session preferably comprises a number of exercises, each exercise preferably comprises a number of sets, and each set preferably comprises a number of reps. A rep is generally defined a one complete cycle through a given exercise. For example, the rehabilitation protocol includes the exercise of a lunge. A patient performing the lunge preferably cycles through lunge forward, hold, lunge back, and relax. The patient then starts over with the next lunge forward. Each cycle through the steps of the lung exercise, e.g., forward, hold, back, relax, is preferably a repetition of that exercise.

By breaking the rehabilitation protocol into phases, the clinician can specify goals that are safe for a given phase. For example, the clinician may wish to specify lower goals directly following an injury or medical procedure. These lower goals may be directed toward simply moving the involved area. Then, after a clinician-specified time, the firmware will indicate to the patient that they have reached another phase with potentially higher goals. Thus, the firmware is flexible and provides the clinician with the ability to progressively set goals for the patient.

Moreover, the rehabilitation protocol may vary the exercises associated with a given phase. For example, an initial phase may vary in the types and frequency of exercises from that of a phase associated with an almost-recovered patient. According to the preferred embodiment, the clinician custom tailors each rehabilitation protocol to the particular needs and limitations of the patient from the clinician software. The custom-tailored rehabilitation protocol is loaded into the monitoring device 210 such that the firmware guides the patient through the exercises associated with each phase. The firmware then records data associated with the patient's performance, and, stores this data for eventual upload to the clinician system 215.

According to another embodiment, the firmware may advantageously determine when to proceed to another phase by monitoring the extent that the patient reaches the clinician-recommended goals for the current phase. According to this embodiment, the patient remains in a given phase until some percent of the goals associated with the exercises in that phase are accomplished to a predetermined extent. When the firmware recognizes that the patient is continually meeting the goals, the firmware may recommend or automatically increment the phase. On the other hand, the firmware may advantageously decrement the phase based on patient progress.

According to another embodiment, phase advancement is controlled by the clinician. In this embodiment, the clinician may recommend phase advancement after viewing uploaded performance data. On the other hand, the clinician may approve phase advancement by simply speaking with a patient. According to one embodiment, phase advancement is protected by a password that the clinician provides to the patient after giving approval to advance. According to another embodiment, the clinician may set a flag in the clinician system 215 that is downloaded to the monitoring device 210 such that the monitoring device 210 advances the phase.

FIGS. 4A–4F illustrate exemplary flowcharts of the firmware loaded into the memory 235 of the monitoring device 210. FIGS. 4A–4F illustrate representative features of the firmware and a skilled artisan will recognize from the disclosure herein that other aspects and features may be incorporated therein. For example, a data integrity check, such as for example, a checksum, may be routinely employed to monitor data and program integrity. Further, the particular data flows used to communicate with the clinician system 215, the setting and enabling of alarms, and the like may also be incorporated into the firmware.

Figure 4A:
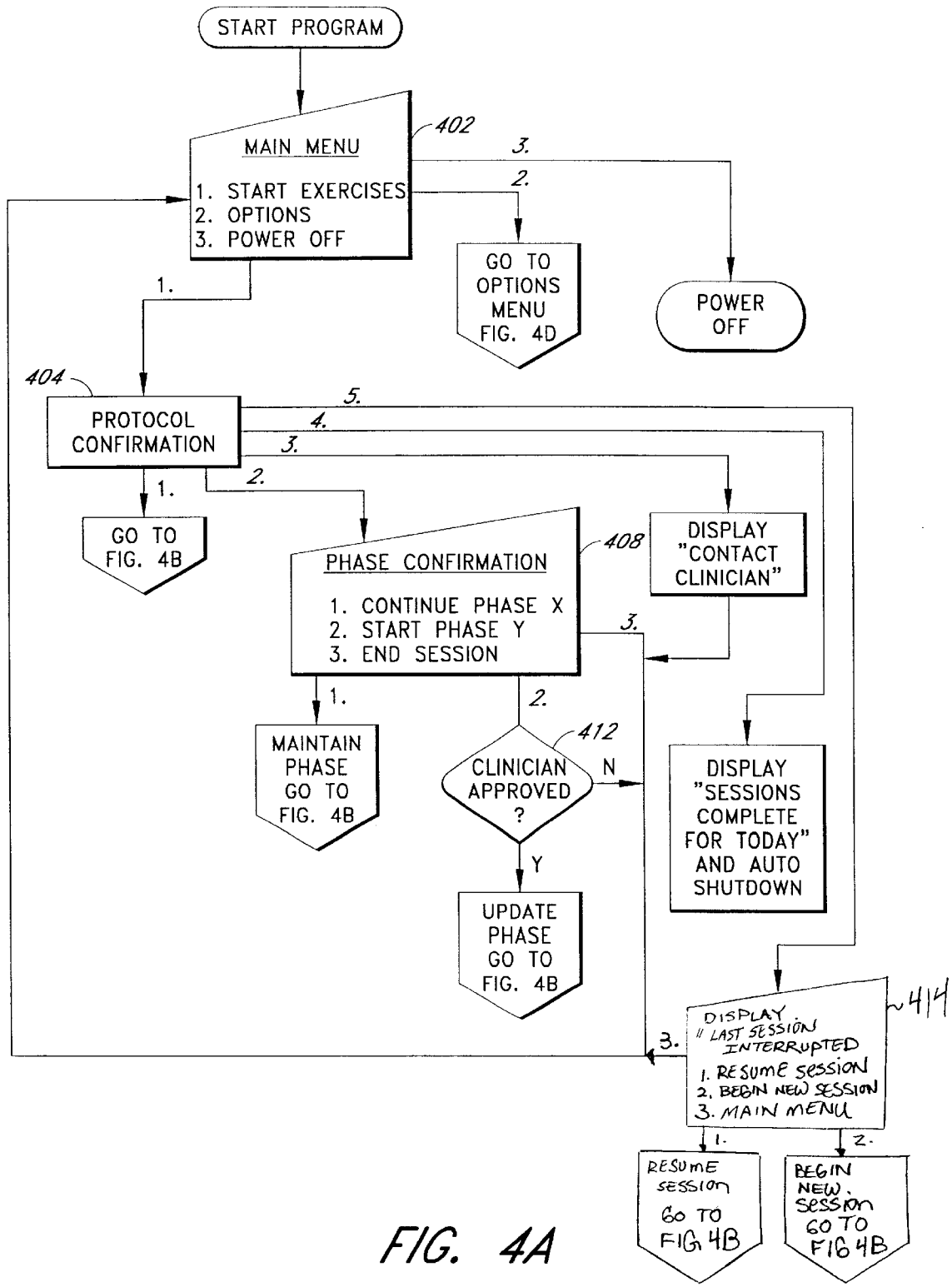
FIGS. 4A–4F illustrate exemplary flowcharts of the firmware, according to aspects of an embodiment of the invention.

FIG. 4A illustrates an exemplary flowchart of the power-on process beginning with Step 402 displaying the Main Menu screen. The Main Menu screen allows an operator, for example, the patient or clinician, to choose to "START EXERCISES," view "OPTIONS," or "POWER OFF." When the operator chooses to "START EXERCISES," the firmware proceeds to Step 404, and executes Protocol Confirmation. Here, the firmware confirms one of five rehabilitation protocol states. The first state includes the rehabilitation protocol being present and at the beginning of an exercise session. When the firmware confirms that the rehabilitation protocol is in the first state, the firmware is forwarded to FIG. 4B.

The second state includes the rehabilitation protocol being present and the current day being greater than the prescribed days for the current phase. When the firmware confirms that the rehabilitation protocol is in the second state, the firmware proceeds to Step 408 and displays the Phase Confirmation screen. In the Phase Confirmation screen, the operator may choose to "CONTINUE PHASE X," "START PHASE Y," or "END SESSION." When the operator chooses to "CONTINUE PHASE X," or in other words, continue with the current phase, the firmware maintains the current phase and is forwarded to FIG. 4B. When the operator chooses to "START PHASE Y," or in other words, to proceed to the next phase, the firmware, at Step 412, determines whether progression to the next phase has been approved by the clinician. Such determination preferably is made by prompting the operator. When the operator indicates clinician approval, the firmware preferably updates the phase and is forwarded to FIG. 4B. On the other hand, if the operator indicates that he or she does not have clinician approval, the firmware is forwarded to the Main Menu screen of Step 402.

According to an alternative embodiment, the firmware may advantageously determine clinician approval at Step 412 through a number of differing mechanisms. As mentioned in the foregoing, the monitoring device 210 may communicate with the clinician system 215 to obtain such approval. Alternatively, the rehabilitation protocol may advantageously contain preapproval or provide a list of exercise milestones that are required for approval to move to the next phase. Such milestones may include, for example, a number of sessions or days meeting various exercise goals. The monitoring device 210 may also request a clinician-provided password before moving to the next phase.

Returning to the Phase Confirmation screen at Step 408, when the operator chooses "END SESSION," the firmware is forwarded to the Main Menu screen of Step 402.

The third state of the rehabilitation protocol, determined by the firmware in the Protocol Confirmation of Step 404, includes the protocol not being present in the memory 235, or otherwise unavailable to the microcontroller 230. When the firmware confirms that the rehabilitation protocol is in the third state, the firmware preferably displays "No Exercise Program is Loaded, Contact Clinician," and is forwarded to the Main Menu screen of Step 402. The fourth state of the rehabilitation protocol includes the exercise sessions for the current day being complete. When the firmware confirms that the rehabilitation protocol is in the fourth state, the firmware displays "All Sessions Complete for Today," and performs AutoShutdown. The AutoShutdown process preferably includes pausing for a predetermined time, and then powering-off the monitoring device 210. The Protocol Confirmation of Step 404 may also determine that the last exercise session was interrupted.

Figure 4B:
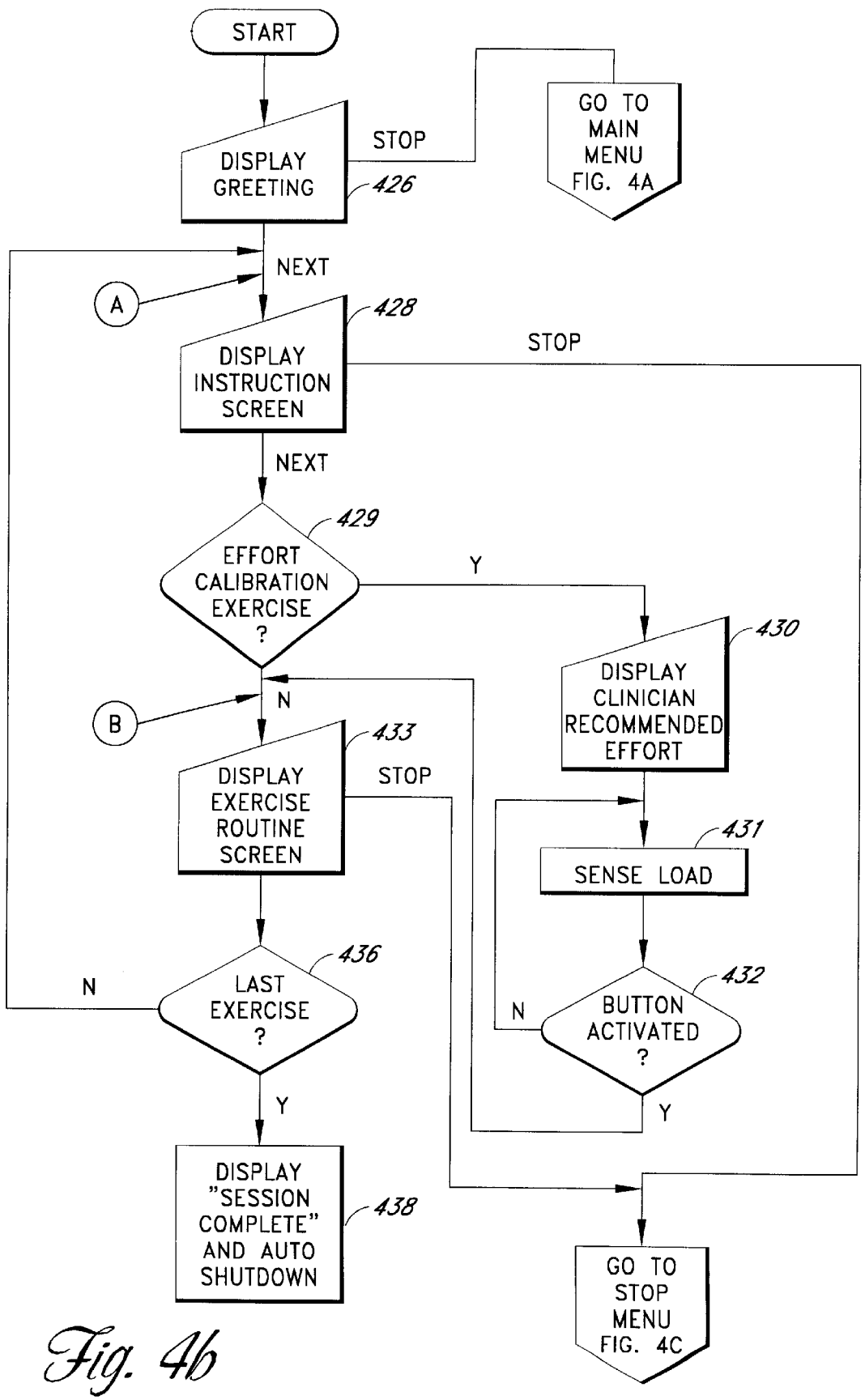

When the firmware determines the rehabilitation protocol is in this fifth state, the firmware, at Step 414, preferably displays the Session Interrupted screen and the text "Last Session Interrupted." In the Session Interrupted screen, the operator may choose to "RESUME SESSION," "BEGIN NEW SESSION," or "MAIN MENU." When the operator chooses to "RESUME SESSION," the firmware maintains the current session and is forwarded to FIG. 4B. When the operator chooses to "BEGIN NEW SESSION," the firmware increments the current session to preferably the next session and is forwarded to FIG. 4B. On the other hand, when the operator chooses "MAIN MENU," the firmware is forwarded to the Main Menu screen of Step 402.

Figure 4C:
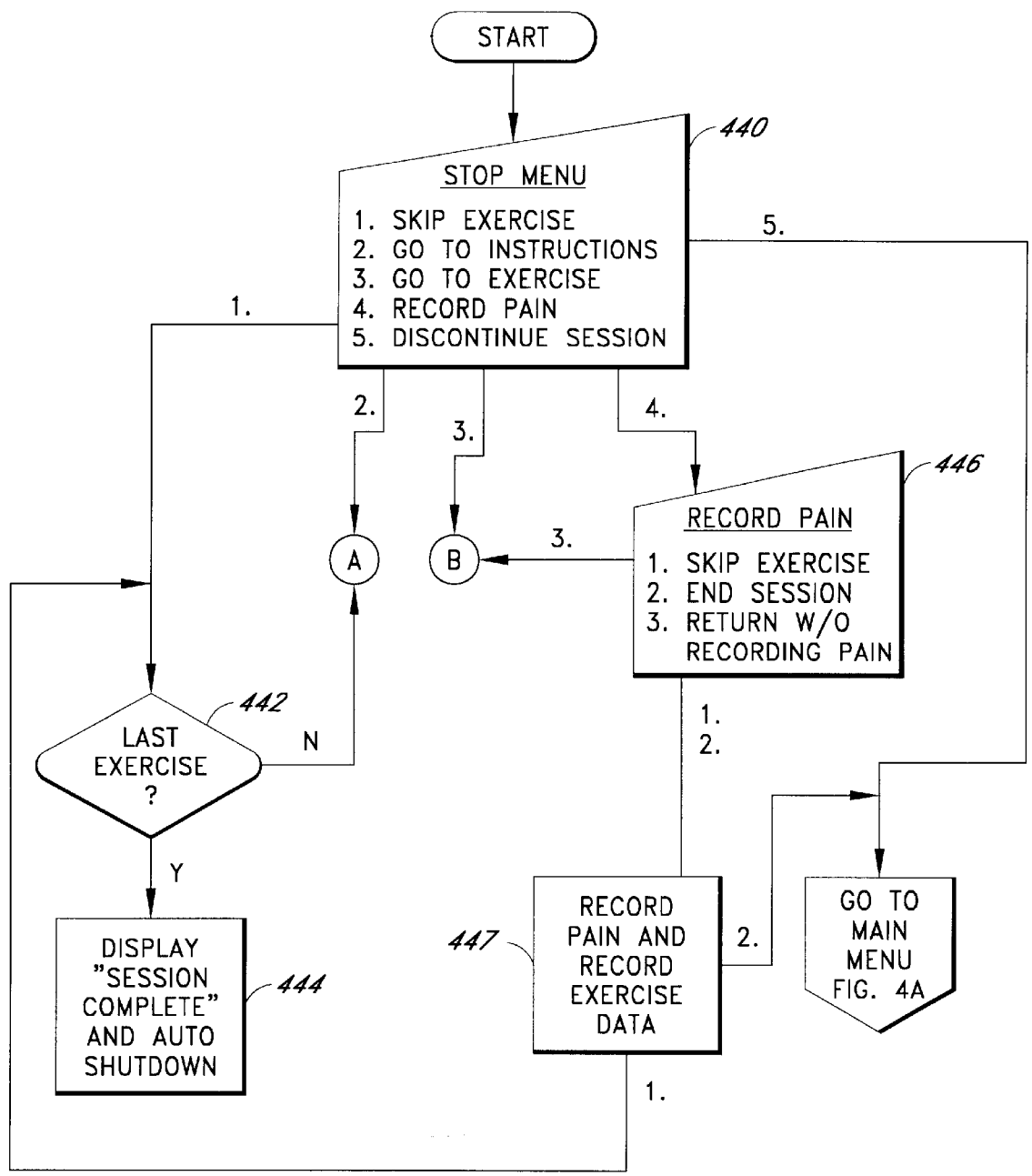
Figure 4D:
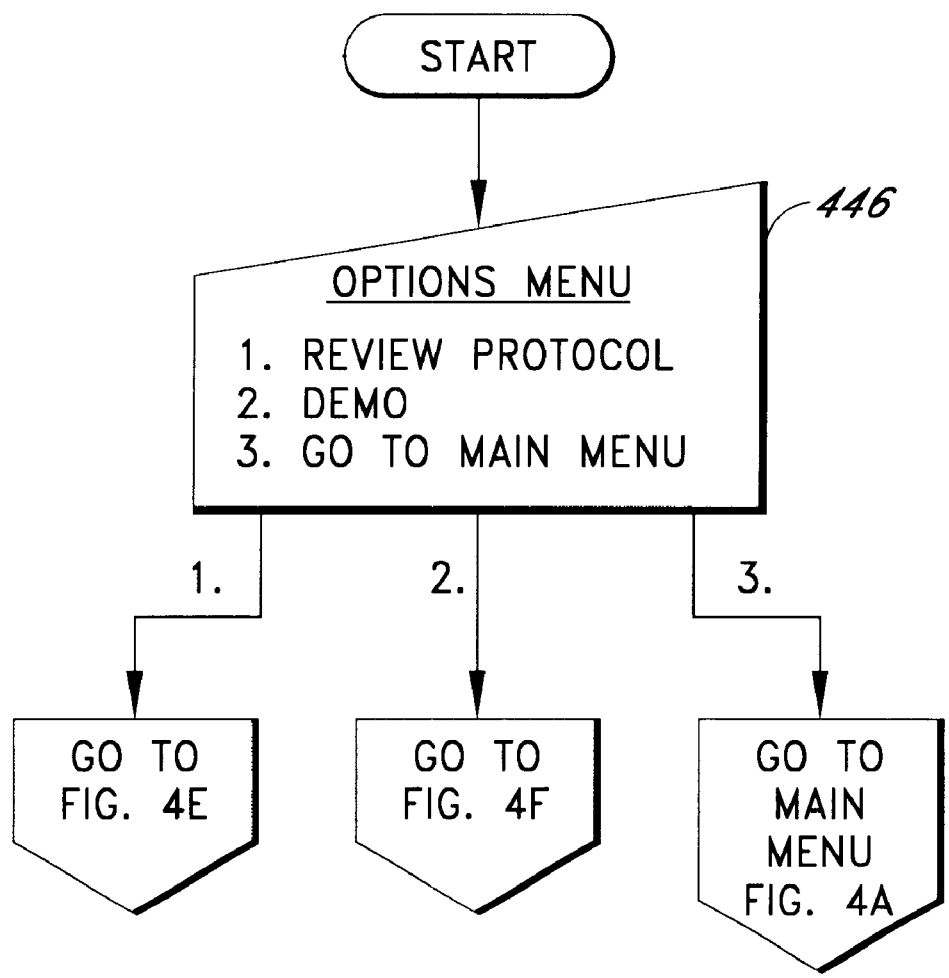

Returning to the Main Menu screen at Step 402, the operator may also choose to view "OPTIONS." When the operator makes this selection, preferably the firmware is forwarded to the Options Menu of FIG. 4D. On the other hand, when the operator chooses "POWER OFF" from the Main Menu screen, the firmware powers-off the system.

FIG. 4B illustrates an exemplary flowchart of the exercise mode process, beginning with Step 426, displaying the Greeting screen. According to the preferred embodiment, the Greeting screen advantageously displays the current phase, day, and session of the rehabilitation protocol for the patient operating the monitoring device 210. The operator preferably selects "NEXT" or "STOP" at Step 426. When the operator selects "NEXT", the firmware proceeds to Step 428 and displays the Instruction screen. When the operator selects "STOP", the firmware is forwarded to the Main Menu screen of Step 402. The Instruction screen preferably provides the operator with text and graphics instructing the operator how to perform the current exercise. Such instruction may advantageously include providing clinician-recommended exercise goals, recommended settings for the brace hinge assembly 205, recommended timing for each step of the exercise, and the like. According to another embodiment of the invention, during the Instruction screen, the firmware may advantageously produce audio signals to be output to the audio/visual output 245. The audio signals may advantageously provide audio instructions corresponding to, and/or supplementing, the text and graphic instructions.

According to the preferred embodiment, at any time during the Instruction screen, the operator may select "NEXT" to proceed, or "STOP". When the operator selects "STOP", the firmware is forwarded to the Stop Menu screen of FIG. 4C.

When the operator selects "NEXT", the firmware proceeds to Step 429 and determines whether the current exercise includes effort calibration. Effort calibration advantageously provides the clinician with the ability to normalize the rehabilitation protocol to an individual patient's abilities. For example, for exercises including effort calibration, the clinician recommends a percentage effort as the patient's goal, as opposed to, or in addition to, an absolute goal. According to the preferred embodiment, the isometric exercises advantageously include effort calibration. Thus, during an isometric exercise, the brace hinge assembly 205 is typically locked at a recommended angle and the patient is instructed to flex or extend such that a torque is applied to the locked brace hinge assembly 205. In addition, the patient is preferably instructed to flex or extend at a percentage of maximum effort. The monitoring device 210 records this effort and sets the recorded data as the goal for a particular set, session, day, phase, or protocol.

Although the invention is disclosed with reference to the preferred embodiment, a skilled artisan will recognize from the disclosure herein that the effort calibration may advantageously be extended to one or more parameters of one or more exercises. For example, the clinician may prescribe percentage efforts to the number of sets, reps, resistance, loads, angles, hold times, relax times, or the like, for each exercise in the rehabilitation protocol, thereby normalizing the parameters and exercises to individual patients.

Moreover, the foregoing normalization using effort calibration advantageously streamlines clinician development of protocols. For example, using the effort calibration, clinicians may develop template protocols having exercises assigned to each session, day and phase. The exercise may advantageously use effort calibration so as to normalize the templates to large numbers of patients having similar injuries. Thereafter, clinicians advantageously use small modifications for fine tuning of the protocol to the individual.

When the firmware determines, at STEP 429, that the current exercise includes effort calibration, the firmware is forwarded to Step 430. At Step 430, the firmware preferably displays the clinician recommended percentage effort, such as, for example, "Use thirty percent of maximum effort." During an isometric exercise, the patient then applies what they perceive as the clinician recommended percentage effort. During the application, the firmware employs, at Step 431, the angle sensor 220 in the case of range of motion exercises, or the load sensor 225 in the case of isometric exercises, to detect the respective angle or torque placed on the brace hinge assembly 205. The operator is preferably instructed to activate the input device 250 to indicate to the monitoring device 210 that the angle or torque being sensed corresponds to their perception of the clinician recommended percentage effort. At Step 432, the firmware determines if the input device 250 has been activated. For example, the firmware may determine whether one of the buttons has been pushed. If so, the firmware sets the current value of the angle or torque as the value of the clinician recommended goal, thereby calibrating the exercise to the clinician recommended percentage effort.

Thereafter, the firmware proceeds to Step 433 and displays the Exercise Routine screen for the current exercise. On the other hand, if the firmware determines, at Step 432, that the input device 250 has not been activated, the firmware returns to Step 431 and continues to sense the current angle or torque applied by the patient.

According to another embodiment of the invention, the foregoing effort calibration may advantageously occur in the clinician's presence. According to such an embodiment, the clinician encourages the operator to perform an exercise, such as, for example, to exert a force against the brace or to move through a range of motion. As the clinician encourages the operator, the clinician preferably activates the input device 250, thereby calibrating the monitoring device 210 for the exercise.

Returning to Step 429, when the firmware determines that the current exercise does not include effort calibration, the firmware proceeds to Step 433 and displays the Exercise Routine screen for the current exercise.

According to the preferred embodiment, the exercise routine screen guides the operator through the current exercise with a variety of text, graphic, and timing indicia being displayed. Preferably, the text, graphics, and timing indicia provide progressive goals, motivation, and other informative functions. For example, the text preferably corresponds to the instructions and clinician-recommended parameters. The graphics preferably provide a progressive goal, an indication of proper body position, and an indication of actual body position. The difference in the indication of proper body position and actual body position provides visual feedback to guide and correct the operator's performance of the current exercise. The timing preferably integrates with the text and graphics to provide a pace or metronome-like function for the exercise.

According to the preferred embodiment, the firmware includes a rehabilitation protocol including exercises that can be selectively assigned by the Clinician. For example, the clinician may assign certain exercises to a given phase and session, and other exercises to another phase or session. Moreover, the exercises may be assigned based on the realization of clinician recommended goals. Further, for each exercise, the Exercise Routine screen preferably adapts and changes to accommodate each exercise associated with the expanded rehabilitation protocol. For example, the Exercise Routine screen may advantageously comprise a pacing screen, a threshold detection screen, a progressive goal screen, or a dynamic target screen. TABLE 1 illustrates an example of a flexible and expanded rehabilitation protocol organized by exercise category and indicating the preferred Exercise Routine screen employed by the firmware.

TABLE 1

REHABILITATION PROTOCOL

| EXERCISE CATEGORY | EXERCISE TITLE | EXERCISE ROUTINE SCREEN |
| --- | --- | --- |
| Patella Mobilization | Patella Mobilization | Pacing |
| Range of Motion | Ankle Pump | Pacing |
| | Towel Roll | Pacing |
| | Prone Hang | Pacing |
| | Heel Slide | Progressive Goal |
| | Wall Slide | Progressive Goal |
| | Flexion Prone | Progressive Goal |
| | Assisted Passive ROM Flexion | Progressive Goal |
| | Assisted Passive ROM Extension | Progressive Goal |
| Isometrics | Multiangle Quad Set | Threshold Detection |
| | Multiangle Ham Set | Threshold Detection |
| | Multiangle Isometric Quadricep | Progressive Goal |
| | Multiangle Isometric Hamstring | Progressive Goal |
| | Multiangle Co-contractions | Pacing |

TABLE 1-continued

REHABILITATION PROTOCOL

| EXERCISE CATEGORY | EXERCISE TITLE | EXERCISE ROUTINE SCREEN |
|---|---|---|
| Non-weight bearing | Hip Abduction | Pacing |
| | Hip Adduction | Pacing |
| | Hip Extension Prone | Pacing |
| | Hip Flexion Supine | Pacing |
| | Knee Extension Sitting | Progressive Goal |
| | Knee Flexion Sitting | Progressive Goal |
| Weight bearing | Squat | Progressive Goal |
| | Lunge Forward | Pacing |
| | Lunge Lateral | Pacing |
| | Step Up | Pacing |
| | Step Down | Pacing |
| | Heel Raise | Pacing |
| Neuromuscular Re-Education | Weight Bearing | Dynamic Target |
| | Non-Weight Bearing | Dynamic Target |

During the Exercise Routine screen, the operator may, at any time, select "STOP", and the firmware is forwarded to the Stop Menu screen of FIG. 4C. On the other hand, when the operator completes the exercise, i.e., the operator performs the recommended repetitions and sets, the monitoring device 210 saves the data associated with the exercise to the memory 235, and in particular to the flash memory, such that it will not be erased.

In particular, the firmware stores the performance data preferably after the completion of each set, however, a skilled artisan well recognized from the disclosure herein a wide number of suitable times to store data, such as for example, after each rep, set, session, day, or phase. Preferably, after the operator completes the reps and sets of the current exercise, the firmware proceeds. However, according to one embodiment of the invention, before proceeding, the firmware provides visible recognition to the operator when the operator has completed the rep, set, session, day, or phase, of the current exercise.

Thereafter, the firmware determines, at Step 436, whether the just-completed exercise was the last exercise for a session. When the just-completed exercise is the last exercise for a session, the firmware, at Step 438, displays "SESSION COMPLETE" and then performs AutoShutdown. Alternatively, when the just-completed exercise is not the last exercise for a session, the firmware is forwarded to the Instruction screen of Step 428. The firmware then provides the operator with instructions corresponding to the next exercise corresponding to the current phase, day, and session of the rehabilitation protocol.

According to another embodiment of the invention, between the operator finishing the exercise, at Step 433, and the firmware determining whether the session includes another exercise, at Step 434, the firmware displays a Progress screen. The Progress screen advantageously displays data relating to the performance progress of the operator. For example, the data may include progressive data saved for a given exercise over a session or number of sessions, a day or number of days, a phase or number of phases. The data may also include comparisons among various exercises. Moreover, according to one embodiment, the firmware may select data from differing sessions, days, phases, and/or exercises such that the data presented is the data most likely to motivate the patient to progress beyond prior performance. For example, such data may correspond to those exercises that the patient accomplished the clinician-recommended progressive goals.

Although the foregoing exercise mode process is disclosed with reference to its preferred embodiments, a skilled artisan will recognize other embodiments of the invention from the disclosure herein. For example, the effort calibration of Step 429 may advantageously calibrate a percentage effort once per set, per exercise, per session, per day or per phase. According to one preferred embodiment, the effort calibration of Step 429 advantageously calibrates the percentage effort once per session. Moreover, the calibration may advantageously be reused even when the clinician recommendation changes. For example, when effort calibration is conducted at, for example, fifty percent effort, and the clinician recommendation changes to ninety percent-effort, the firmware may advantageously mathematically compute the new goal. On the other hand, the firmware may average other effort calibrations or simply recalibrate according to Steps 429–432.

FIG. 4C illustrates an exemplary flowchart of the stop menu process, beginning with Step 440, displaying the Stop Menu screen. According to the preferred embodiment, the Stop Menu screen allows the operator to choose from various selections corresponding to rationale for terminating an exercise session. For example, the Stop Menu preferably includes "SKIP EXERCISE," "GO TO INSTRUCTIONS," "GO TO EXERCISE," "RECORD PAIN," and "DISCONTINUE SESSION." When the operator chooses to "SKIP EXERCISE," the firmware determines whether one or more repetitions of the current exercise have been performed. If so, the data corresponding to the one or more fully performed repetitions is preferably stored. In addition, at Step 442, the firmware preferably determines whether the just-completed exercise was the last exercise for a session. When the just-completed exercise is the last exercise for a session, the firmware, at Step 444, displays "SESSION COMPLETE" and then performs AutoShutdown. When the just-completed exercise is not the last exercise for a session, the firmware is forwarded to the Instruction screen of Step 428 of FIG. 4B, where the firmware displays instructions corresponding to the next exercise.

Returning to the Stop Menu screen, the operator may also choose to "GO TO INSTRUCTIONS." When the operator makes this selection, the firmware is forwarded to the Instruction screen of Step 428 of FIG. 4B, where the firmware displays the instructions corresponding to the current exercise. The "GO TO INSTRUCTIONS" selection advantageously allows the operator the ability to review the instructions during an exercise without having to progress through an iteration of the exercise. For example, the operator can review the instructions without recording data associated with an exercise that the operator was not sure how to properly perform.

The operator may also choose from the Stop Menu screen the selection of "GO TO EXERCISE." When the operator makes this selection, the firmware is forwarded to the Exercise Routine screen of Step 433 of FIG. 4B. By providing the "GO TO EXERCISE" selection, the firmware advantageously allows the operator the ability to return and finish the current exercise after pausing for any of a wide number of reasons. For example, the operator may pause for a phone call, visitor, interrupting child, or the like.

The operator may also choose to "RECORD PAIN" from the Stop Menu screen. When the operator makes this selection, the firmware, at Step 446, presents the operator with the Record Pain screen. According to the preferred embodiment, the Record Pain screen presents the following options to the operator: "SKIP EXERCISE," "END SESSION," and "RETURN WITHOUT RECORDING PAIN." When the operator selects "SKIP EXERCISE" or "END SESSION" from the Record Pain screen, the firmware is forwarded to Step 447 and preferably records that the operator has felt pain. According to one embodiment, the operator may advantageously be prompted to rate the magnitude of pain according to a scale, and/or enter a general or precise location of where the pain was felt. Such information may advantageously be used to suggest a course of action, including returning to the exercise session, contacting the clinician, and/or adjusting goals, phases, and the like. According to a preferred embodiment, when the operator has performed one or more repetitions of an exercise before recording pain, the data corresponding to the one or more fully performed repetitions is stored along with the fact that the operator felt pain.

When the operator records pain at Step 447 and has chosen to "SKIP EXERCISE," the firmware is then forwarded to Step 442 where it determines whether the just-skipped exercise is the last exercise. On the other hand, when the operator records pain at Step 447 and has selected "END SESSION," the firmware is forwarded to the Main Menu screen of Step 402 of FIG. 4A. When the operator selects "RETURN WITHOUT RECORDING PAIN" from the Record Pain screen, the firmware is preferably forwarded to the Exercise Routine screen of Step 433 of FIG. 4B.

FIG. 4D illustrates an exemplary flowchart of a few options available to the operator for customizing the monitoring device 210. The flowchart begins with Step 446, where the firmware displays the Options Menu screen. According to the preferred embodiment, the Options Menu screen preferably includes a "REVIEW PROTOCOL" "DEMO," and "GO TO MAIN MENU" selections. When the operator selects "REVIEW PROTOCOL," the firmware is forwarded to FIG. 4E. When the operator selects "DEMO," the firmware is forwarded to FIG. 4F. And, when the operator selects "GO TO MAIN MENU," the firmware is forwarded to the Main Menu screen of Step 402, FIG. 4A.

Figure 4E:
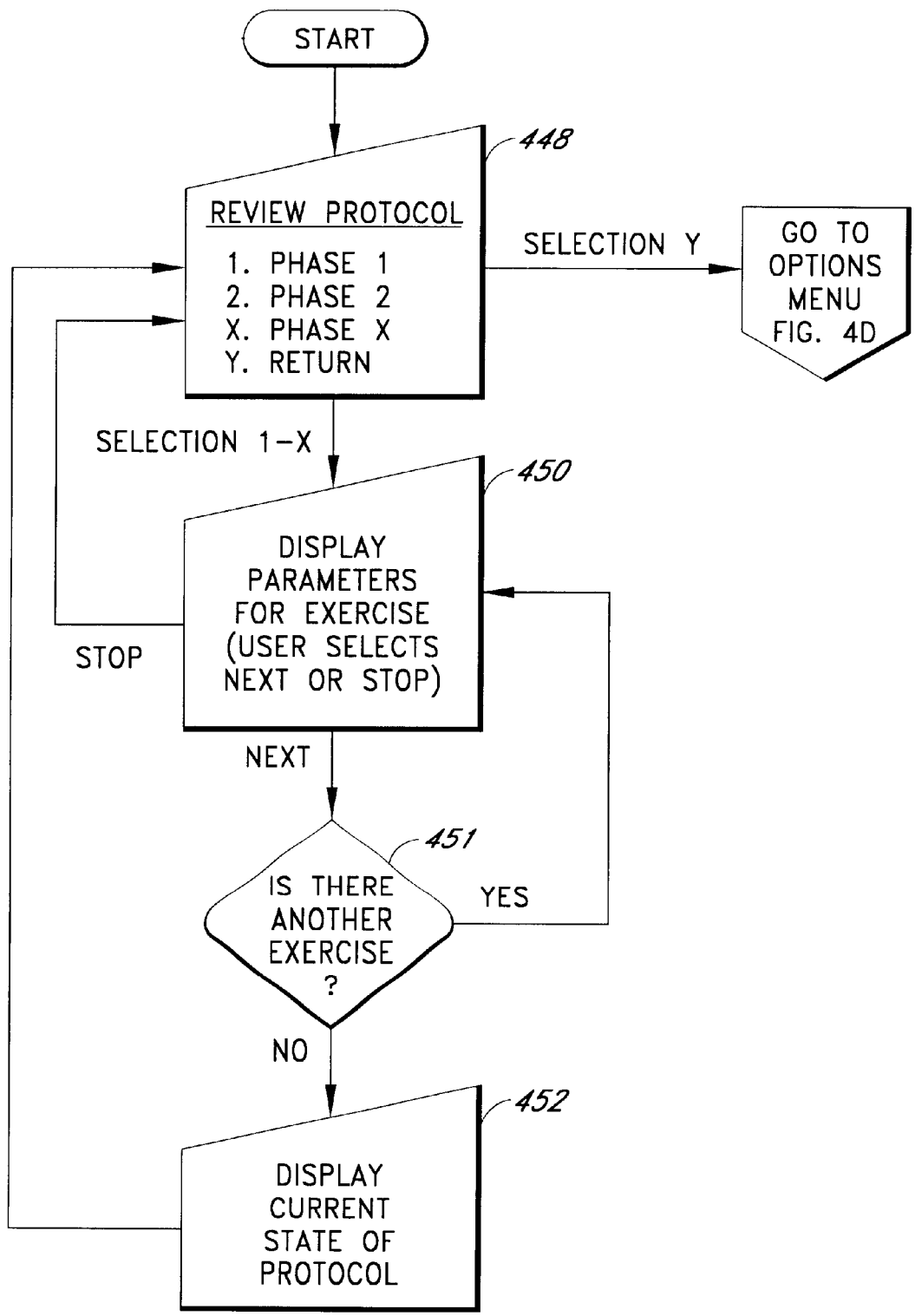

FIG. 4E illustrates an exemplary flowchart of a review rehabilitation protocol process, beginning with Step 448, displaying the Review Protocol screen. Providing the review rehabilitation protocol process advantageously allows the operator to quickly review the protocol loaded into the monitoring device 210 to ensure that the protocol was properly loaded, and that the patient has possession of the monitoring device 210 having his or her protocol loaded thereon. For example, in clinics where many monitoring devices similar to the monitoring device 210 may be handled on a daily basis for checkout, protocol downloads, data uploads, and the like, the clinician or the patient may quickly and efficiently use the Review Protocol screen to ensure the proper device is provided to the proper patient. Moreover, the review rehabilitation protocol process provides the operator the ability to quickly review the clinician recommendations for a given exercise, such that the operator may quickly configured the brace hinge assembly 205 or otherwise prepare for performance of an exercise.

According to the preferred embodiment, the Review Protocol screen allows the operator to select a particular phase for review or return to the Option Menu screen of Step 446 of FIG. 4D. When the operator selects a phase to review, the firmware, at Step 450, displays the first exercise and its parameters associated with the operator-selected phase.

After reviewing the first exercise and its respective parameters, the operator may select "Next," or "Stop." Selecting "Stop" returns the firmware to the Review Protocol screen at Step 448 where the operator may again choose a phase to review or choose to return to the Options Menu screen. Selecting "Next" at Step 450 forwards the firmware to Step 451 where the firmware determines if there is another exercise assigned to the operator-selected phase. If there are more exercise assigned to the given phase, the firmware returns to Step 450 and displays the next exercise and its associated parameters. On the other hand, if there are no more exercise in the operator-selected phase, the firmware proceeds to Step 452 where it preferably displays information pertaining to the current state of the rehabilitation protocol. For example, firmware may advantageously display the current date time, phase, day, session, set, rep, or the like. After displaying the current state of the rehabilitation protocol, the firmware returns to Step 448 where the operator may choose another phase or return to the Options Menu of FIG. 4D.

Figure 4F:
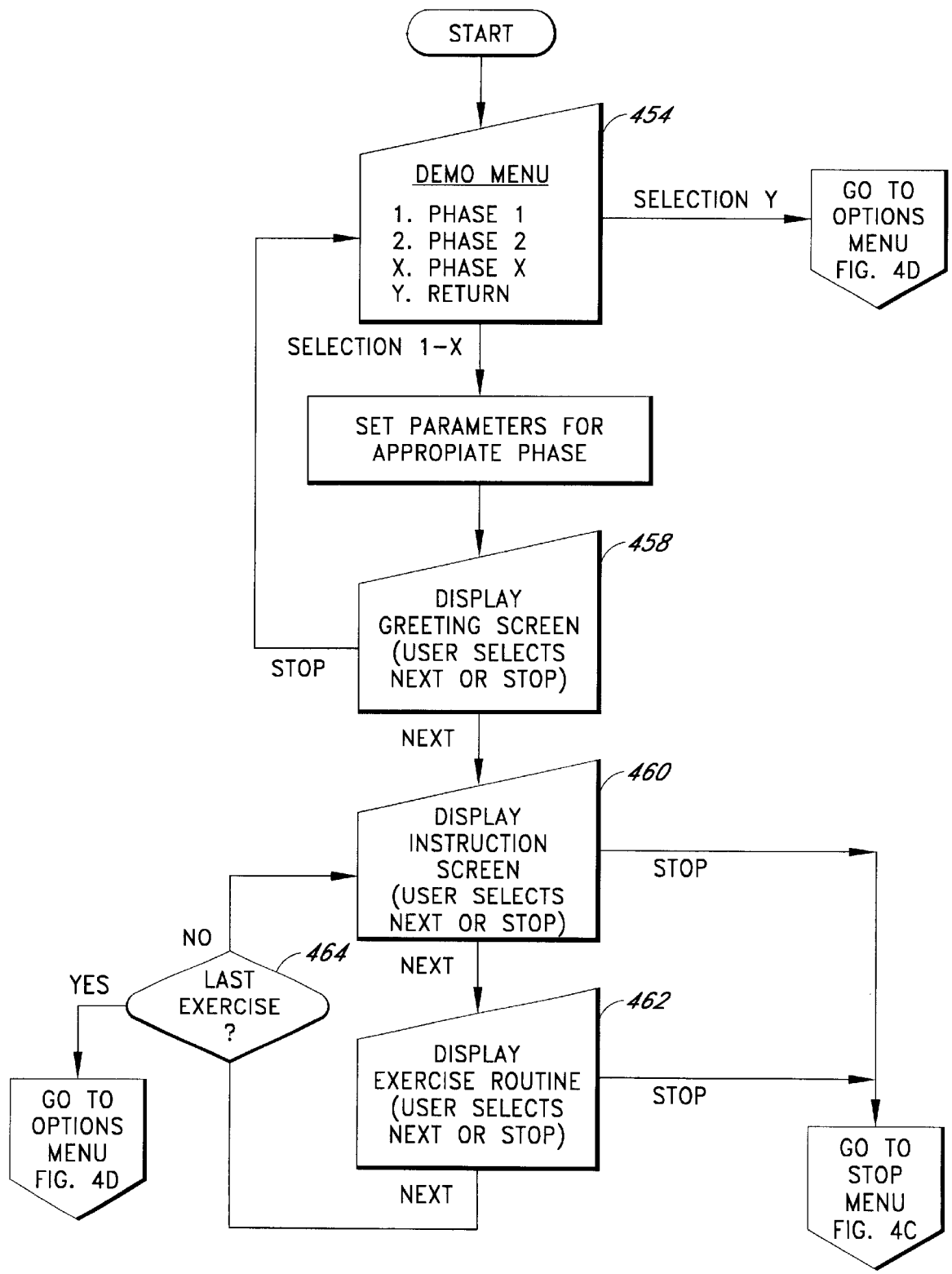

FIG. 4F illustrates an exemplary flowchart of a demo mode according to the preferred embodiment of the invention. The demo mode advantageously provides for demonstration and training on the use of the device for the patient by the clinician or clinician staff without recordation of the associated performance data. According to the preferred embodiment, the demo mode process begins with Step 454, displaying the Demo Menu screen. The Demo Menu screen preferably allows the operator to either select a phase for demonstration, or return to the Options Menu screen of FIG. 4D. When the operator selects a phase to demonstrate, the firmware is forwarded to Step 456 where the parameters are set for the exercises associated with the operator-selected phase. Preferably, the firmware automatically pulls the parameters and exercises for the selected phase from the rehabilitation protocol loaded on the system. However, according to one embodiment of the invention, the parameters and exercises associated with the selected phase may advantageously be entered at Step 456. Such operator entry allows for demonstration of the system without having a rehabilitation protocol loaded thereon.

After the firmware has the parameters for the operator-selected phase, the demo mode process proceeds through steps similar to those of the exercise mode process of FIG. 4B. For example, the demo mode process includes Step 458, displaying the Greeting screen, Step 460, displaying the Instruction screen, Step 462, displaying the Exercise Routine screen, and Step 464, determining whether the just-performed exercise is the last exercise. Unlike FIG. 4B, the demo mode process returns to the Options Menu screen of FIG. 4D when the firmware determines the just-performed exercise is the last exercise of the operator-chosen phase. Similar to FIG. 4B, the demo mode process allows the operator to interrupt the demo mode process during Steps 460–462 and proceed to the Stop Menu screen of FIG. 4D.

According to one preferred embodiment, the demo mode process includes the effort calibration steps of FIG. 4B, preferably between Steps 460 and 462. According to another embodiment, the demo mode process includes displaying a Progress screen for displaying performance information about the data stored in the memory 235 of the monitoring device 210.

Although the demo mode process is similar to that of the exercise flow of FIG. 4B, the demo mode process of FIG. 4F preferably does not record performance data or "use up" the rehabilitation protocol for the selected phase and exercise. For example, although the preferred embodiment pulls the clinician-recommended parameters for the selected phase and exercise, the demo mode process does not count the demonstration as a performance of that exercise. Therefore, the demonstration advantageously allows for instruction without disadvantageously using memory or initiating day one of the rehabilitation protocol. On the other hand, according to a second embodiment the performance data may be temporarily stored during a demonstration such that the Exercise Routine screen, and when appropriate, the Progress screen, have access to past performance data. According to this embodiment, when the operator exits the demo mode process, the performance data is erased from, or otherwise overwritten in, the memory 235.

THE CLINICIAN SYSTEM

The clinician system 215 preferably includes application software for tracking patient information, for developing and assigning rehabilitation protocols to patients, and for generating reports from uploaded patient performance data. The patient information may be entered at the outset of treatment, or advantageously be retrieved from other medical institutions, such as, for example, the referring hospital, surgeon, or primary health care provider's system.

Figure 5:
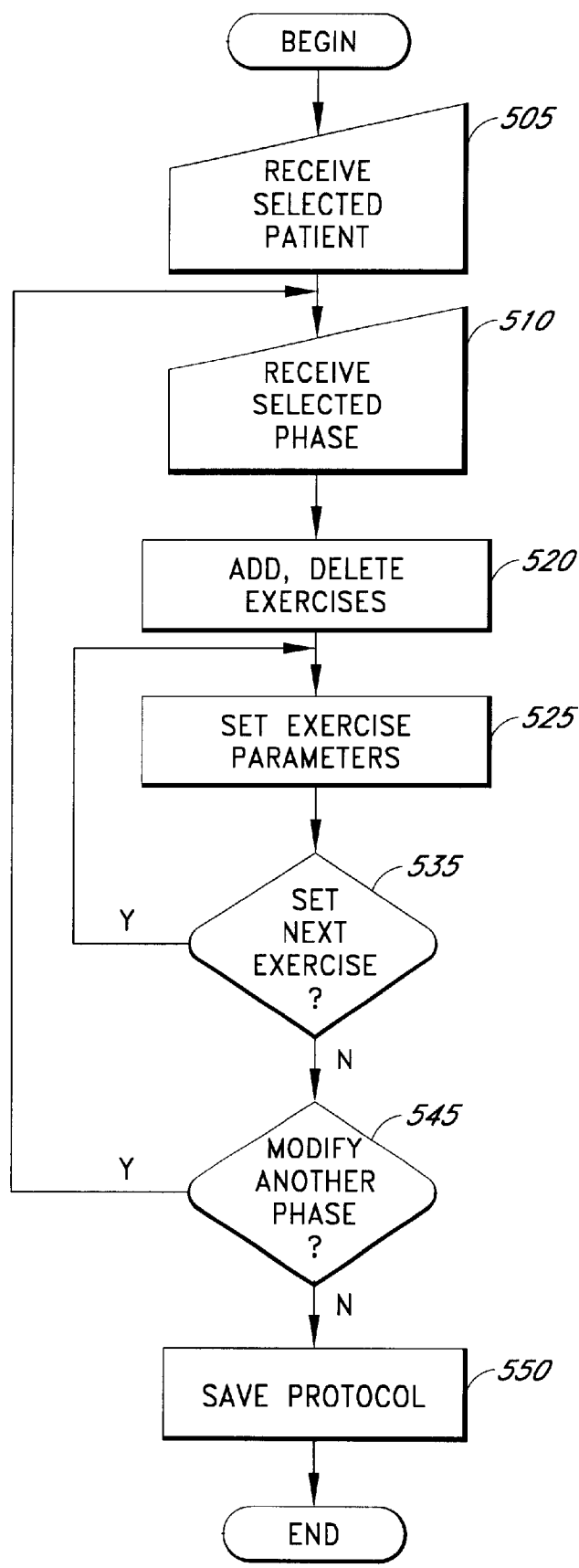
FIG. 5 illustrates an exemplary flowchart of a protocol development process of the clinician software, according to aspects of an embodiment of the invention.

FIG. 5 illustrates an exemplary flowchart of the protocol development process implemented in the application software for assigning and developing rehabilitation protocols for patients. As shown in FIG. 5, the protocol development process begins at Step 505 by receiving from the clinician system operator, the selection of a patient from the database of patients. Alternatively, the protocol development process may receive the entry of a new patient. At Step 510, the protocol development process receives the clinician system operator's selection of a phase for modification. In Step 520, the clinician system operator interacts with the protocol development process, such that the clinician system operator advantageously adds and deletes exercises associated with the selected phase, resulting in a list of exercises assigned to the phase. At Step 525, the clinician system operator preferably sets exercise parameters for one of the exercises in the list for the selected phase. The exercise parameters preferably include recommendations relating to the reps, sets, maximum angles or torque, lock and limit settings, resistance values, pacing information, effort calibration, or the like, for each exercise.

In addition to the foregoing, one embodiment of the invention includes the clinician system operator setting the number of sessions during a day that the patient is to perform the selected exercise. Thus, through the protocol development process, the clinician system operator may advantageously tailor a rehabilitation protocol such that a phase includes a number of days having the same exercise routine, and each of those days may advantageously have a differing set of exercises assigned to differing sessions. Moreover, each exercise may include different recommendations for any of the foregoing parameters.

After setting the exercise parameters for one exercise, the clinician system operator may choose, at Step 535, to set exercise parameters for another exercise assigned to the current phase. When the clinician system operator so chooses, the protocol development process returns to Step 525. On the other hand, when the clinician system operator does not choose to set exercise parameters for another exercise assigned to the current phase, the clinician system operator may choose, at Step 545, to modify exercises in another phase. If so, the protocol development process returns to Step 510 where the operator performs the foregoing modifications to the exercises of another phase. On the other hand, if the operator is finished working with the rehabilitation protocol, then the rehabilitation protocol is saved at Step 550 in the clinician system 215 and the protocol development process ends.

A skilled artisan will recognize from the disclosure herein a wide number of alternative processes to develop the foregoing rehabilitation protocol. For example, the operator may load a partially completed protocol and begin customization from a particular point forward. On the other hand, the operator may store template protocols, and edit only those exercises and parameters needed to better suit a particular patient. Moreover, the clinician may use default exercise parameters, default exercise associations with a given phase, day, and session, or partial templates for particular phases, days or sessions, or combinations of the foregoing.

The clinician system 215 also includes applications for reporting performance data. Once performance data is uploaded from the monitoring device 210, the clinician system 215 preferably offers reporting capabilities to the clinician. For example, the clinician system 215 may offer complete performance histories showing all performance data, preferably along with the clinician prescribed recommendations, and when applicable, the effort calibrations. On the other hand, the clinician system 215 may advantageously group subsets of the entire performance history. For example, the clinician system may advantageously provide compliance data only, compliance exceptions only, performance progress, or combinations of the foregoing.

The clinician system 215 may also perform statistical analysis, multipatient comparisons, or data norm comparisons. Data norm comparisons preferably compare the recorded performance from the monitoring device 210 with that of preconsidered "normal" performance results. Such normal results may include healthy patient performances, similarly-suited patient performances, or the like.

In addition, the clinician system 215 preferably allows the operator to specify date ranges for which reports are generated. For example, the clinician system operator may specify a given time period for which reports should be generated, such as, for example, the previous month, week, or number of weeks.

Thus, based on the foregoing, the clinician system 215 provides the clinician system operator with the flexibility to customize and normalize rehabilitation protocols for patients. In addition, the clinician system 215 communicates with the monitoring device 210 to download the customized protocols and upload resulting performance data. The clinician system 215 also preferably generates efficient, customizable reports from the performance data provided.

PROGRESSIVE GOALS AND EXEMPLARY SCREEN SHOTS

Figure 6:
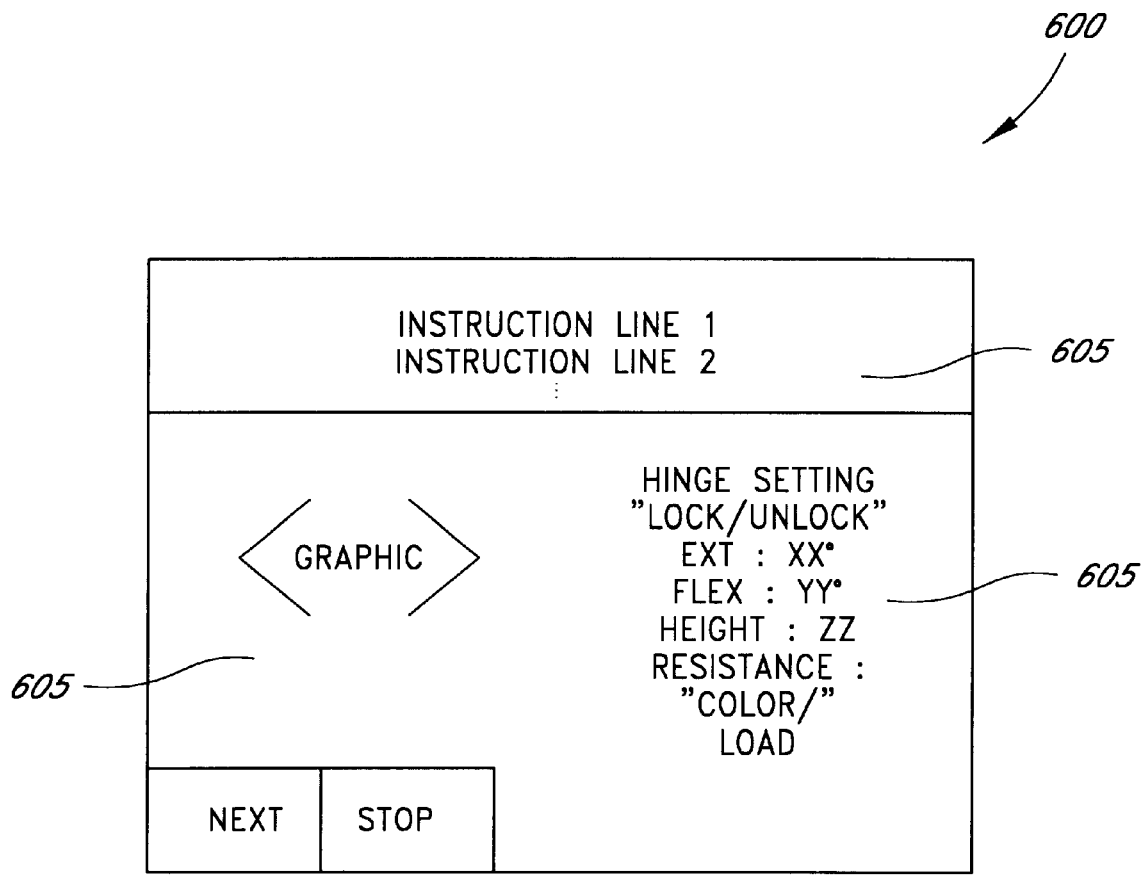
FIG. 6 illustrates the content of an exemplary instruction screen, according to the firmware of FIGS. 4A–4F.

FIG. 6 illustrates the content of an exemplary instruction screen 600, according to the foregoing Instruction screen of Step 428 of FIG. 4B. As shown in FIG. 6, the instruction screen 600 comprises three sections, an instruction section 605, a parameter section 610, and a graphics section 615. Preferably, the firmware uses the instruction section 605 to present textual information relating to instructions for the current exercise. According to the preferred embodiment, the instruction section 605 scrolls text such that regardless of the amount of text, the size of the instruction section 605 does not change. For example, the instruction section 605 may comprise a horizontal frame in the instruction screen 600. However, a skilled artisan will recognize from the disclosure herein that the instruction section 605 may comprise a wide number of differing formats and presentation styles. The parameter section 610 preferably includes a listing of the clinician-recommended parameters for the current exercise. Such recommendations may advantageously include resistance settings or colors, extension/flexion angles, lock angles, step height recommendations for step exercises, and the like. Preferably, the parameters are implemented such that they include particular information for a given orthopedic brace. For example, according to the preferred embodiment, the parameters include settings for the visible indicia 335 of the brace 205, along with various resistance settings and step height recommendations. The graphic section 615 of the instruction screen 600 comprises animated graphics preferably supplying instructional information. The instructional information may advantageously include real-time feedback of loads or angles from the angle sensor 220 and load sensor 225. The instructional information may also include timing instructions such as pacing for various exercises. The pacing preferably is depicted through the rate of change in the graphics and/or the textual information presented in the instructional screen 600.

Figures 7A, 7B:
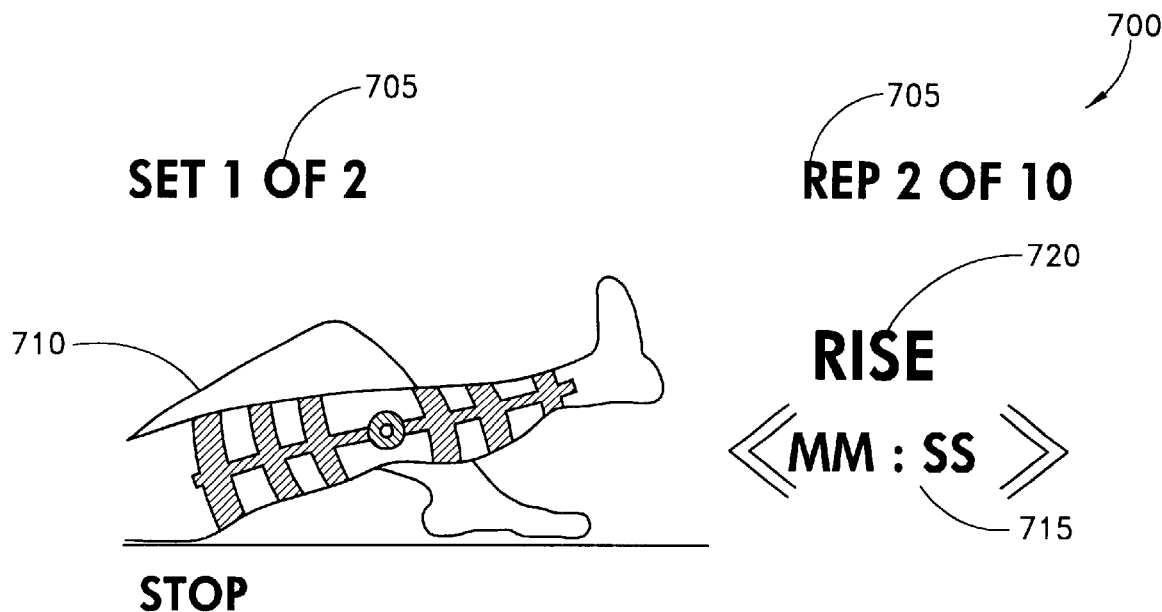
FIG. 7A illustrates the content of an exemplary pacing exercise screen, according to the firmware of FIGS. 4A–4F.
FIG. 7B illustrates an exemplary data structure for storing performance data during a pacing exercise, according to aspects of an embodiment of the invention.

FIG. 7A illustrates the content of an exemplary pacing exercise screen 700, according to the Exercise Routine screen of FIG. 4B. The firmware preferably employs the pacing exercise screen 700 when a particular exercise focuses on the pace of the performance or the exercise does not provide a load or angle variation that can be sensed by the brace sensors. For example, the patella mobilization exercise of TABLE 1, where the patient is to use his or her hand to physically move the patella in four directions, typically does not supply a load or an angle variation on the brace hinge assembly 205. However, clinicians typically use the patella mobilization exercise near the beginning of rehabilitation to help the patient first begin moving the involved knee. By using the monitoring system 200 for pacing exercises, the clinician can take advantage of features of the monitoring system 200 other than the sensors of the brace hinge assembly 205. For example, during the patella mobilization exercise, the clinician preferably employs the instruction screen 600, the pacing exercise screen 700, and the memory 235. Thus, according to the preferred embodiment, even exercises that do not employ the sensors are programmed into the monitoring system 200 in order to utilize the other advantages provided thereby. For example, some measure of compliance can be judged by measuring time alone.

As shown in FIG. 7A, the pacing exercise screen 700 preferably includes counters 705 for tracking the repetitions, sets, and the like, during an exercise. Moreover, the pacing exercise screen 700 comprises a graphic 710, a stopwatch 715 and a mode indicator 720. The graphic 710 comprises animation associated with the exercise. For example, for the patella mobilization exercise, the graphic 710 changes such that it paces and instructs the patient by including an arrow indicating the clinician-recommended direction and timing of movement, and/or an animation of a knee having the patella moving in the clinician-recommended direction. Such movement preferably corresponds to the clinician-recommended pace.

The stopwatch 715 and the mode indicator 720 preferably work in concert to pace the patient through the exercise. For example, during a co-contraction exercise, where the patient is flexing both the quadriceps and the hamstring muscles, the mode indicator 720 changes modes from "TIGHTEN" to "RELAX." Moreover, the stopwatch 715 preferably includes minutes and seconds such that it counts down the duration of a given mode displayed on the mode indicator 720. Based on the above example, the mode indicator 720 preferably displays "TIGHTEN," while the stopwatch 715 preferably counts down the clinician-recommended seconds of the "TIGHTEN" repetition, thereby pacing the patient through the exercise.

FIG. 7B illustrates an exemplary data structure 750 corresponding to exercises employing the pacing screen 700. As shown in FIG. 7B, the data structure 750 comprises an exercise ID 755, an incomplete/complete status 760, a pain status 765, the current set 770, and for certain exercises, the locked angle 775 of the brace hinge assembly 205, the current rep 780, the maximum extension angle 785 and the maximum flexion angle 790. The exercise ID 755 preferably identifies which of the various exercises the performance data represents, preferably including the phase, day, and session associated therewith. The incomplete/complete status 760 preferably indicates whether the patient completed the clinician-recommended repetitions. The pain status 765 preferably indicates whether the patient used the Stop Menu screen of FIG. 4C to record pain during the exercise. The current set 770 preferably provides the number of sets performed for the exercise. The locked angle 775 preferably indicates at what angle the brace hinge assembly 205 was locked during the exercise. The current rep 780 preferably indicates the number of current repetitions at the end of a set. For example, if the operator successfully completed all of the repetitions of a set, the current rep 780 would include every repetition. On the other hand, if the operator stopped the exercise to, for example, record pain, the current rep 780 may be a subset of the available reps for the set. The maximum extension/flexion angles 785 and 790 preferably indicate the maximum extension and/or flexion angle of brace hinge assembly 205 during the exercise.

The storage of the foregoing data advantageously focuses on that type of data normally desired by the clinician or physical therapist. For example, rather than storing all sampled datapoints during an exercise, the foregoing data focuses on what the patient accomplished. These data are typically more straightforward in their analysis and they use less storage space in the memory 235 of the monitoring device 210.

Figures 8A, 8B:
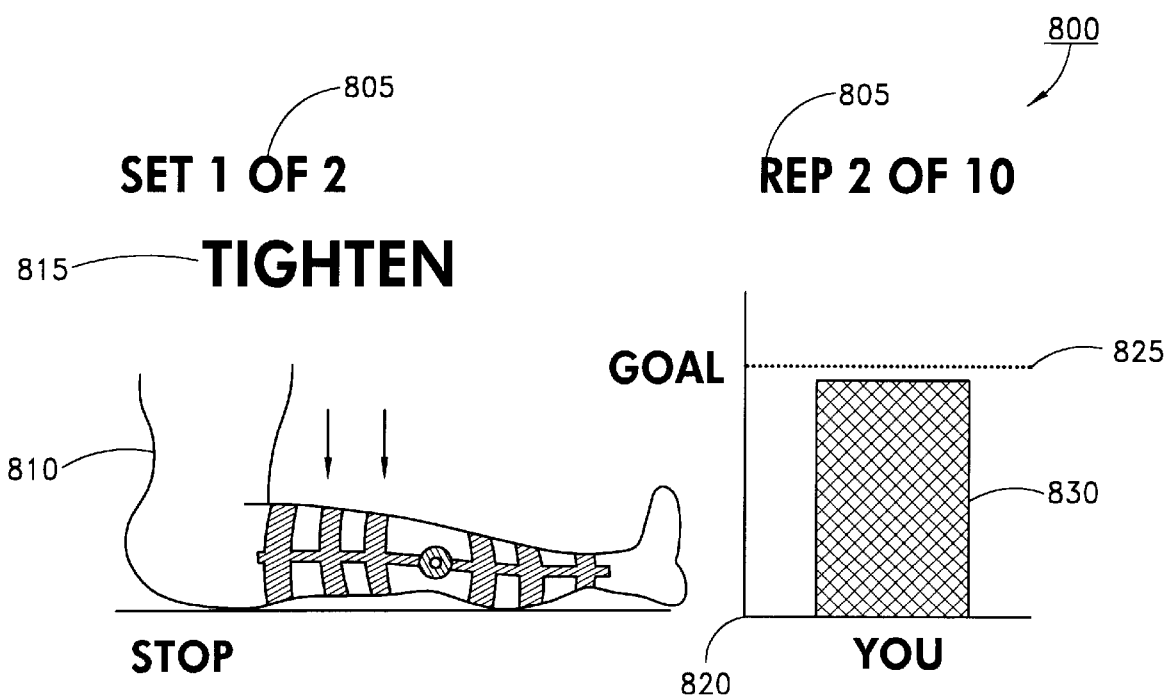
FIG. 8A illustrates the content of an exemplary threshold detection screen, according to the firmware of FIGS. 4A–4F.
FIG. 8B illustrates an exemplary data structure for storing performance data during a threshold detecting exercise, according to aspects of an embodiment of the invention.

FIG. 8A illustrates the content of an exemplary threshold detection screen 800 according to Exercise Routine screen of FIG. 4B. The firmware preferably employs the threshold detection screen 800 when the patient is supposed to contract a muscle for a clinician-recommended amount of time. For example, the multiangle quadricep and hamstring sets of TABLE 1 typically involve the patient locking the brace hinge assembly 205 at a clinician-recommended angle, and then flexing the appropriate muscle groups. Contraction of the muscles will place a load on the locked brace hinge assembly 205 for the recommended time, thus indicating how long the patient held the isometric muscle contraction.

As shown in FIG. 8A, the threshold detection screen 800 includes counters 805 for tracking the repetitions, sets, and the like, during an exercise. Moreover, the threshold detection screen 800 comprises a graphic 810 and a mode indicator 815. The graphic 810 comprises animation associated with the exercise to provide visual instructional and pacing information. The mode indicator 815 preferably paces through modes of "TIGHTEN" to "RELAX." The threshold detection screen 800 also includes a graph 820 having horizontal and vertical axes. Along the vertical axis, the graph 820 includes a horizontal line indicating a goal 825, preferably representing a relatively low torque threshold value. The relatively low threshold is chosen to be above the system noise, yet low enough to sense the muscle contraction. Preferably the threshold is between two Nm and forty-five Nm, and most preferably around four Nm. Along the horizontal axis, the graph 820 includes a meter, or moving bar 830, representing the actual load the patient places on the brace hinge assembly 205. Preferably, the bar rises toward and falls away from the goal based on real-time feedback data from the load sensor 225.

For the exercises employing the threshold detection screen 800, the clinician preferably recommends the duration of the "TIGHTEN" time and a percentage of that duration time where the load sensed should be above the goal 825. If the patient applies a torque or load to the brace hinge assembly 205 for the recommended percentage of time or greater, then the repetition is counted as successful. Thus, the foregoing display of the mode indicator 815 and real-time graph 820 provides visual feedback and encouragement for the patient.

Although the threshold detection screen 800 has been disclosed in terms of a preferred embodiment, a skilled artisan will recognize from the disclosure herein a number of differing visual feedback mechanisms that provide encouragement for the patient. For example, the threshold detection screen 800 may advantageously employ one or a combination of horizontal meters or bars, incrementing and decrementing alphanumerical readouts showing actual values or percentages, or dynamic pie charts representing values or percentages. A skilled artisan will also recognize from the disclosure herein that other pacing features may advantageously be incorporated into the threshold detection screen 800. For example, the stopwatch 715 of FIG. 7A may advantageously count the seconds or percentage of the clinician-recommended "TIGHTEN" time that the patient is above the goal 825. Also, the goal 825 may comprise an angle rather than a load and the patient may attempt to straighten or flex the knee to reach the goal 825. Moreover, the clinician may specify a percentage of effort that the patient should exert during the exercise. The percentage of effort may be displayed as text, or incorporated into the graph 820 as, for example, the goal 825. According to an alternative embodiment, the graph 820 includes a clinician setting as the goal 825, as opposed to the preferred predetermined threshold.

FIG. 8B illustrates an exemplary data structure 850 corresponding to exercises employing the threshold detection screen 800. As shown in FIG. 8B, the data structure 850 comprises elements similar to those of FIG. 7B. In addition, the data structure 850 comprises a lock angle 855 and a number of successfully completed repetitions 860. The lock angle 855 identifies the angle of the brace hinge assembly 205 during the exercise. For example, during the multiangle quad set exercise, the clinician may recommend that the patient perform a number of repetitions or sets at successively incrementing or decrementing knee angles, for example, ten degrees, twenty degrees, etc. In such case, the firmware preferably generates the data structure 850 for each of the locked angles in which the patient performs repetitions or sets of the exercise, and stores performance data, including the locked angle, in the respective data structure 850.

According to the preferred embodiment, the number of successfully completed repetitions 860 indicates the number of repetitions where the patient was able to sustain a load or torque above the goal 825 for the clinician-recommended percentage of the "TIGHTEN" time. As with FIG. 7B, the storage of the foregoing data advantageously focuses on that type of data normally desired by the clinician or physical therapist, thereby creating an efficient storage and transfer of data.

Figures 9A, 9B:
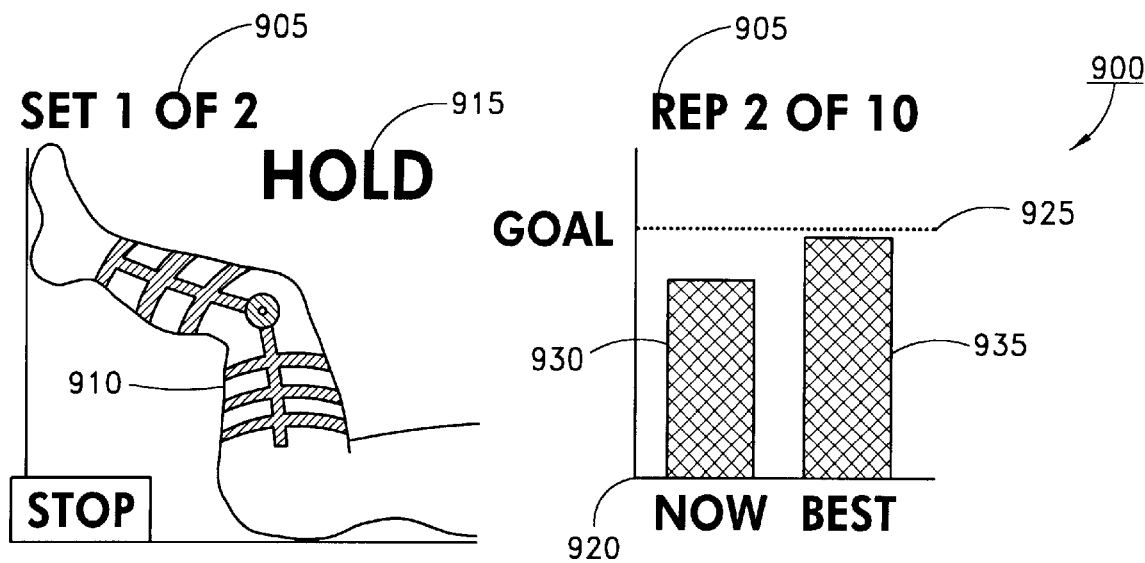
FIG. 9A illustrates the content of an exemplary progressive goal screen, according to the firmware of FIGS. 4A–4F.
FIG. 9B illustrates an exemplary data structure for storing performance data during a progressive exercise, according to aspects of an embodiment of the invention.

FIG. 9A illustrates the content of an exemplary progressive goal screen 900 according to Exercise Routine screen of FIG. 4B. The firmware preferably employs the progressive goal screen 900 to provide safe and productive motivation for the patient. The progressive goal screen 900 includes counters 905 for tracking the repetitions, sets, and the like, during an exercise. Moreover, the progressive goal screen 900 comprises a graphic 910 and a mode indicator 915. The graphic 910 comprises animation associated with the exercise to provide visual instructional and pacing information. The mode indicator 915 preferably paces through modes of "HOLD," "RELAX," and the like. The progressive goal screen 900 also includes a graph 920 having horizontal and vertical axes. Along the vertical axis, the graph 920 includes a horizontal line indicating a goal 925. As discussed in the foregoing, the goal 925 may represent differing types of clinician recommended parameters. For example, according to one embodiment, the goal 925 preferably represents the effort calibration of FIG. 4B. As discussed with reference to FIG. 4B, the effort calibration corresponds to the operator indicating to the firmware through the input device 250 of the monitoring device 210, the value of, for example, a clinician recommended percentage effort. Note that the firmware may advantageously ask the operator to update this value, or as the firmware progresses through increasingly more difficult phases, the firmware may advantageously provide increasingly difficult clinician recommendations. Such recommendations may calibrate automatically from the original percentage effort or may ask the operator to again perform effort calibration.

According to another embodiment, the goal 925 may advantageously include clinician-recommended torque or clinician-recommended extension/flexion angles. According to another embodiment, the goal 925 may comprise clinician recommended percentage effort for some phases and clinician recommended torque or angles for other phases.

The graph 920 also illustrates the horizontal axis having a first meter, or first bar 930 and a second meter or second bar 935. The first bar 930 preferably represents the real-time feedback from the appropriate sensor on the brace hinge assembly 205. For example, during a repetition of the load sensing exercises, the first bar 930 preferably represents the current value of the torque sensed by the load sensor 225. The first bar 930 preferably includes a caption indicating the foregoing, such as, for example, the caption "NOW." The graph 920 also includes the second meter or second bar 935. The second bar 935 represents the peak performance of the repetitions so far completed in the current set of the current exercise. The second bar 935 preferably includes a caption designating the second bar 935 as representing the peak performance of the exercise, such as the caption "BEST."

The data value for the second bar 935 is preferably derived by comparing the current value of the sensors 220 and 225, preferably represented in the first bar 930, with the peak value, preferably represented by the second bar 935. When the current value is greater than the peak value, the peak value is preferably set to the current value. When the current value is less than the peak value, the firmware returns to compare the next value from the sensors 220 and 225 to the peak value.

A skilled artisan would recognize from the disclosure herein that a wide number of possible data representations may advantageously be displayed by the first bar 930 and second bar 935. For example, the first bar 930 may represent the peak performance during a rep of the current set of the current exercise. For example, during an extension exercise, the first bar 930 may represent the smallest angle reached during the extension rep. Moreover, the second bar 935 may represent the peak performance of a given exercise over some or all repetitions, sets, sessions, days, and phases.

Based on the foregoing, the progressive goal screen 900 advantageously employs both real-time feedback along with past performance to motivate the patient to do progressively better with each iteration of each exercise. For example, use of the second bar 935 to represent past performance, provides the patient with a progressive goal in-between the goal 925 and the current performance. The progressive goal continually approaches, and may surpass the clinician-recommended goal, as the patient strives to perform just a little better than the last iteration. By incorporating the information of past performance and current performance into one display screen, the operator is advantageously motivated to do increasing better.

According to another embodiment of the invention, the first bar 930 indicating the current value of the performance of an exercise, may advantageously include a first section and a second section. The first section may represent the actual sensed load or angle the patient places on the brace hinge assembly 205 while the second section may represent the peak performance of the current rep or set of the current exercise. Use of different texture, brightness, color, outline or the like may advantageously visually differentiate the two sections. According to the preferred embodiment, the first section may cover the second section to the extent that the load or angle currently placed on the brace overcomes the peak performance of the current rep or set, or in other words, the value of second section. In such case, the second section adjusts to the new peak performance, and when the current performance, represented in the first section falls below the new peak performance, the differing texture of the second section returns at the new peak performance.

FIG. 9B illustrates an exemplary data structure 950 corresponding to exercises employing the progressive goal screen 900. As shown in FIG. 9B, the data structure 950 comprises elements similar to those of FIGS. 7B and 8B. In addition, the data structure 950 comprises a set-up load 955, a maximum peak torque 960, and an average peak torque 965. The set-up load 955 preferably identifies the value set by the patient during the effort calibration of FIG. 4B. Note that the set-up load may advantageously store a set-up angle in the embodiment providing for effort calibration during range of motion exercises.

The maximum peak torque 960 and the average peak torque 965 preferably indicate the maximum and peak torque or loads applied to the brace 205 during an exercise. As with FIGS. 7B and 8B, the storage of the foregoing data advantageously focuses on that type of data normally desired by the clinician or physical therapist, thereby creating an efficient storage and transfer of data.

Figure 10A:
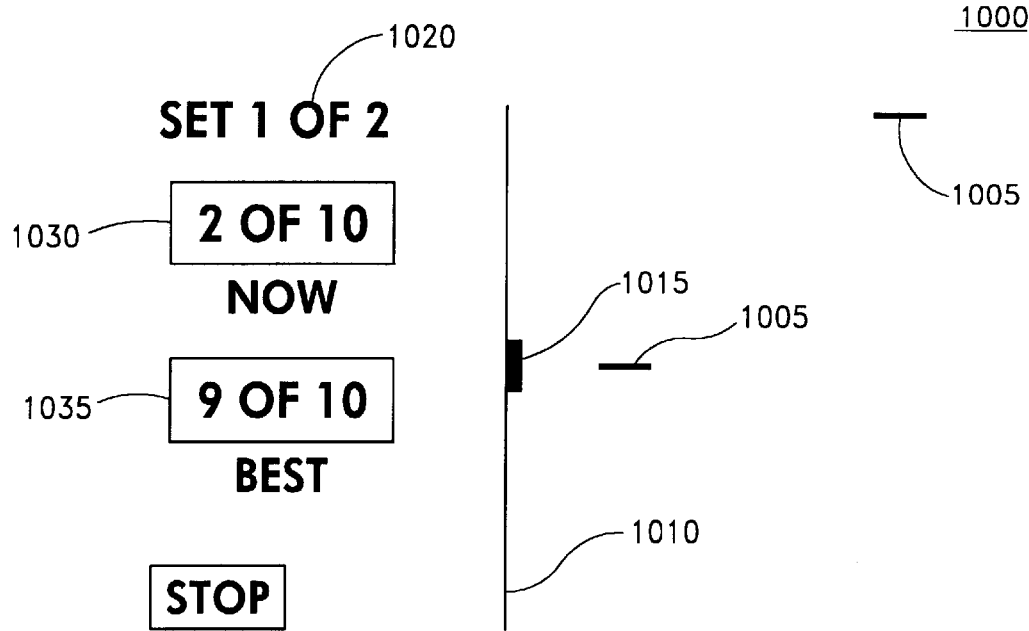
FIG. 10A illustrates the content of an exemplary dynamic target screen, according to aspects of an embodiment of the invention.

FIG. 10A illustrates the content of an exemplary dynamic target screen 1000 according to Exercise Routine screen of FIG. 4B. The firmware preferably employs the dynamic target screen 1000 as a motivational game for improving neuromuscular reeducation. For example, the motivational game preferably involves darts 1005 moving toward a barrier 1010 where the darts 1005 are lost. The game also includes a target 1015 that moves along the barrier 1010. The object of the game is to move the target 1015 in front of the darts 1005, thereby "catching" the darts 1005, before they hit the barrier 1010 and are lost. The patient controls the movement of the target 1015 by applying a torque during isometric configurations or applying angular movement during range of motion configurations. For example, if the clinician recommends that the patient move through a range of motion between ten degrees and forty degrees, the barrier would represent a thirty-degree range of motion. As the patient moved the brace hinge assembly 205 between ten and forty degrees, the target 1015 preferably moves from one extreme to the other.

The dynamic target screen 1000 also includes counters 1020 for tracking the repetitions, sets, and the like, during a game. Moreover, the dynamic target screen 1000 comprises current score 1030 and a best score 1035. Similar to the progressive goal first and second bars, 930 and 935, the current score and best score 1035 preferably represent motivational data such that the patient desires to continually improve his or her performance of the game. Accordingly to the preferred embodiment, the current score 1030 includes alphanumeric text showing how many darts are "caught" during the current game. Similarly, the best score 1035 includes alphanumeric text showing how many darts were caught during a best game. The best game may include a best game from the current or past set, session, day, phase.

Figure 10B:
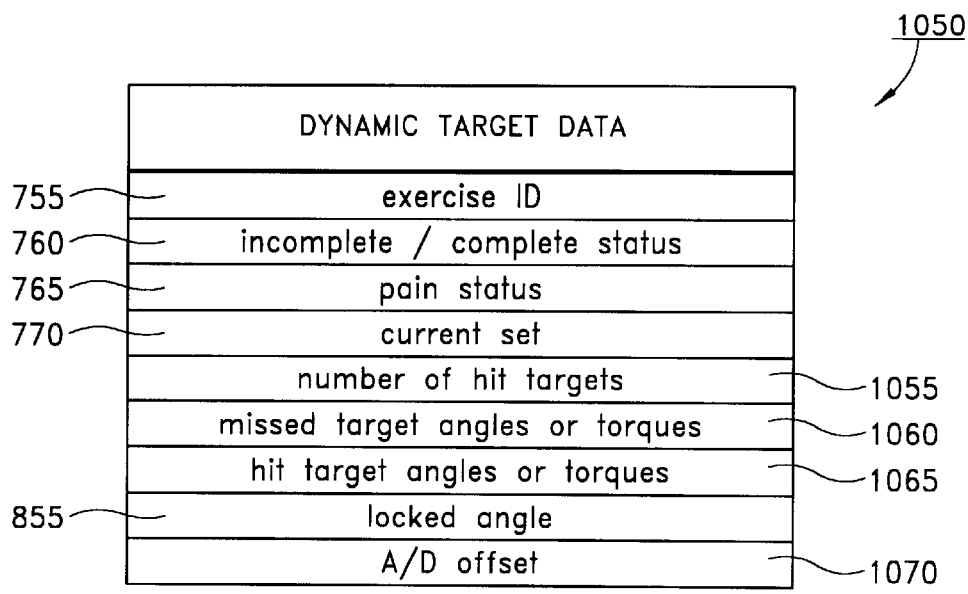
FIG. 10B illustrates an exemplary data structure for storing performance data during a dynamic target exercise, according to aspects of an embodiment of the invention.

FIG. 10B illustrates an exemplary data structure 1050 corresponding to exercises employing the dynamic target screen 1000. As shown in FIG. 10B, the data structure 1050 comprises elements similar to those of FIGS. 7B through 9B. In addition, the data structure 1050 comprises a number of targets hit 1055, missed target angles or torque 1060, hit target angles or torque 1065, and an A/D offset 1070. According to the preferred embodiment, the number of targets hit 1055 comprises the number of darts 1005 caught by the target 1015. In addition, the missed target angles or torque 1060 preferably corresponds to those angles or torque the patient did not reach when a dart 1005 reached the barrier 1010. For example, during a range of motion dynamic target game, if the dart 1005 approached the barrier 1010 at an area where the barrier represented an angle of twenty degrees, and the dart 1005 was not caught by the target 1015, then the firmware preferably stores twenty degrees as a missed target angle 1060. Similarly, the hit target angles or torque 1065 relates to those angles or torque corresponding to darts 1005 caught. Moreover, the A/D offset 1070 comprises a calibration offset for the sensors. For example, at the beginning of an exercise, the monitoring device 210 may advantageously perform a zero calibration. The zero calibration may be performed by measuring a value of the angle sensor 220, the load sensor 225, or both, and set that measurement to correspond to, for example, a null or zero value.

Figure 11:
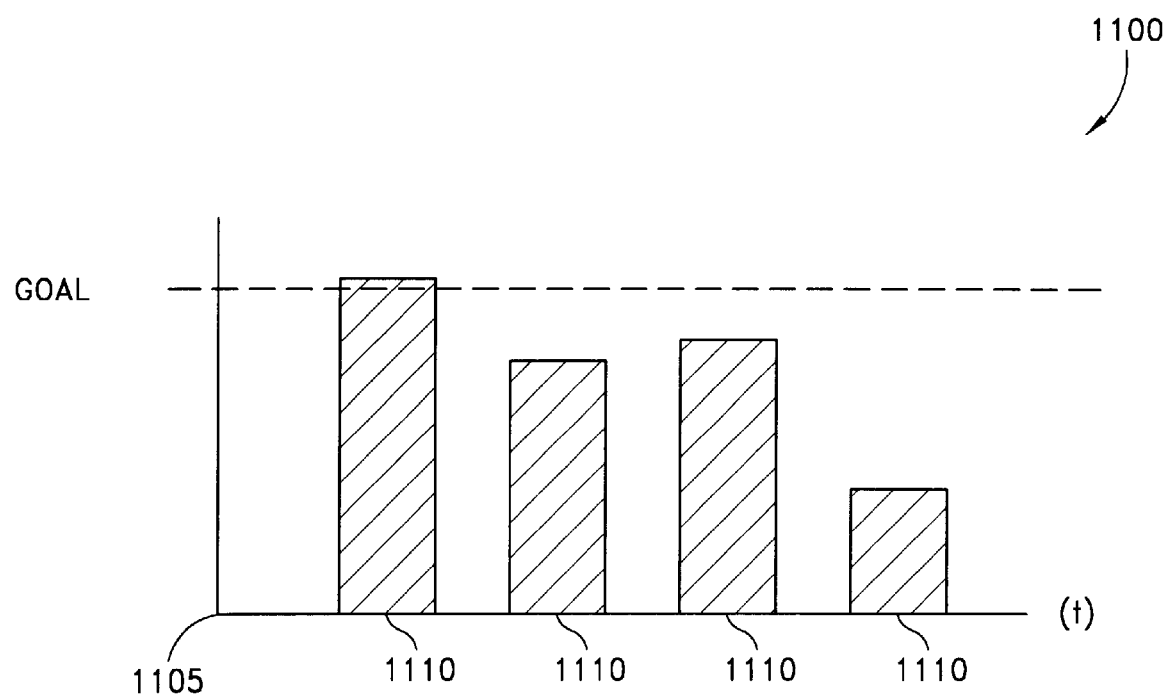
FIG. 11 illustrates the content of an exemplary progress screen, according to the firmware of FIGS. 4A–4F.

FIG. 11 illustrates the content of an exemplary progress screen 1100 according to an alternative embodiment of the exercise flow of FIG. 4B. According to this embodiment, the progress screen 1100 is preferably displayed after the operator finishes an exercise. The operator is then presented with the progress screen 1100 such that past performance data is displayed in a convenient, efficient, and motivational manner. The progress screen 1100 includes a graph 1105 having a vertical axis sized to accommodate the greatest peak load, angle, or the like. The horizontal axis is sized to accommodate a number of recorded past performances. For example, FIG. 11 illustrates the horizontal axis including four meters, or bars 1110 representing the peak performance of the last four sets of the just completed exercise. If four past performances are not available, for example, this is the first iteration of an exercise, the progress screen may advantageously display past performance from other phases, days, sessions, exercises, sets, or the like. If such past performances do not exist, the progress screen may simply show the just-completed peak performance.

Although the foregoing invention has been described in terms of certain preferred embodiments, other embodiments will be apparent to those of ordinary skill in the art from the disclosure herein. For example, a skilled artisan may advantageously recognize a wide number of exercise screens that motivate the patient to perform progressively better. In addition, the skilled artisan may advantageously select various statistics of present and past performance for display in the motivational graphs of the exercise screens. In addition, a skilled artisan would recognize from the disclosure herein that the animation and/or graphics of the various screens may include more or less information, frames, pixels, or the like.

Figure 12:
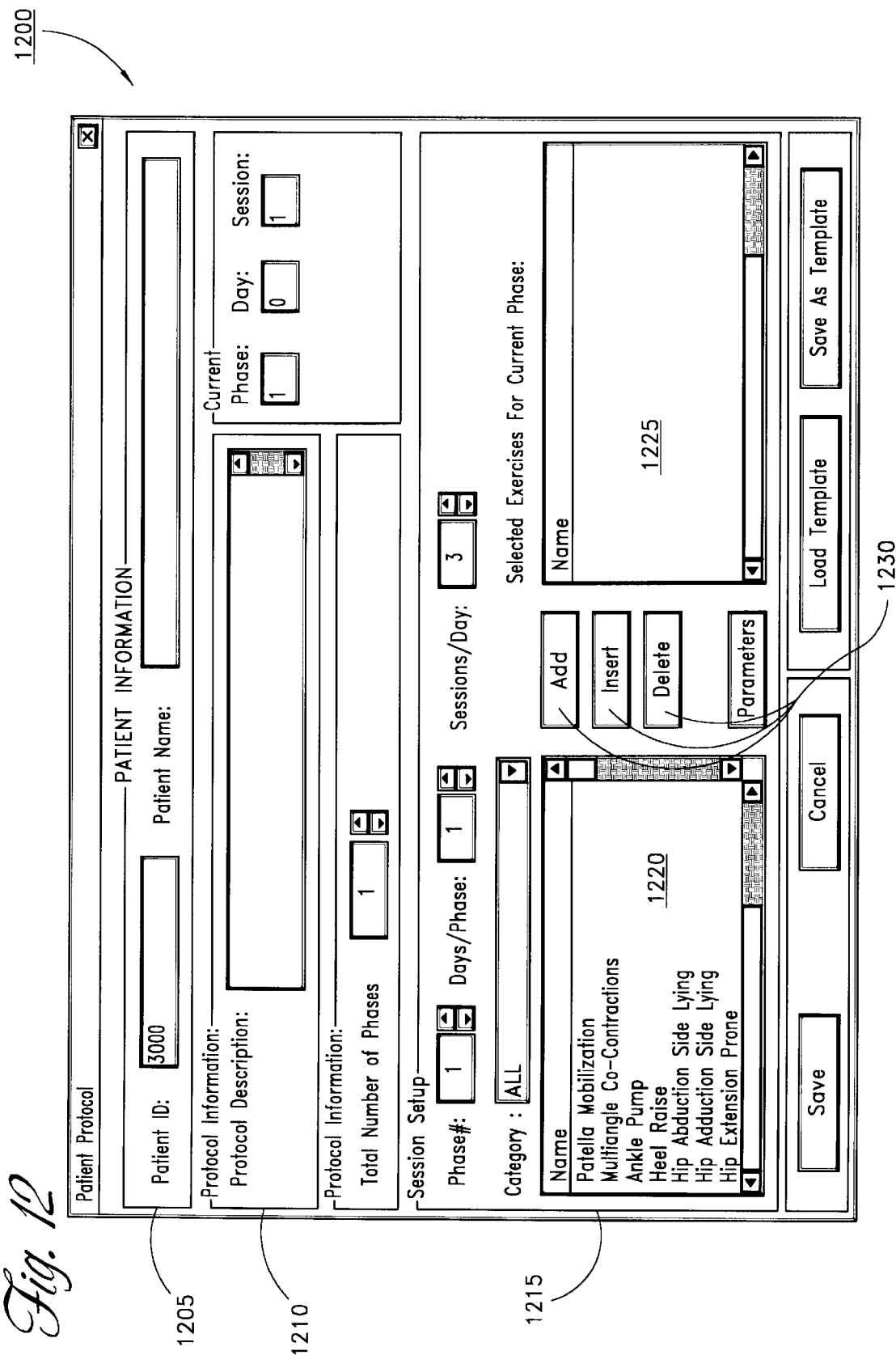
FIG. 12 illustrates an exemplary protocol development screen according to aspects of an embodiment of the invention.

FIG. 12 illustrates an exemplary protocol development screen 1200 of the clinician system 215 according to the protocol development process of FIG. 5. As shown in FIG. 12, the protocol development screen 1200 includes conventional graphical user interface (GUI) windows, buttons, or text boxes, and the like. Moreover, the protocol development screen 1200 includes a patient information section 1205, a protocol information section 1210, and a session setup section 1215. The patient information section 1205 includes information about the current patient, such as, for example, the patient's name, system identification number, medical history, or the like. The protocol information section 1210 includes an optional protocol description and a setting for the number of phases in the current protocol. The setup section 1215 provides the clinician system operator the ability to fully create and customize phases of the current protocol. For example, the setup section 1215 provides a first window 1220 listing some or all of the exercises available for the protocol, and a second window 1225 corresponding to a selected phase, day, and session of the protocol. The clinician system operator uses control buttons 1230, such as, for example, "Add," "Delete," or the like, to move an exercise from the first window 1220 into the second window 1225, thereby assigning the moved exercise to the selected session.

Preferably, when the clinician system operator changes the phase, day, or session, the first window 1220 relists some or all of the exercises available for the protocol. Thus, by removing the exercise from the first window 1220 and placing the exercise into the second window 1225 during assignment to a session, the firmware avoids an inadvertent re-assignment of the same exercise to a session where that exercise already appears in the second window 1225.

As shown in FIG. 12, the control buttons 1230 include a "Parameter" button. According to the preferred embodiment, the clinician system operator may highlight an exercise appearing in the second window 1225, and use the parameter button to edit or input parameters associated with the particular exercise. For example, the parameter may advantageously include the foregoing reps, sets, pacing information, resistances, angles, percentage effort calibrations, and the like.

FIG. 12 also shows the "Save" and "Load" template buttons. The save and load template buttons allow the clinician system operator to save portions or all of a given protocol as a template. Then, when developing a protocol for a given patient, the clinician system operator may advantageously load one or more templates covering one or more phases such that only minor modifications are needed before fully developing the protocol for the individual patient.

Although the invention has been disclosed in its preferred and alternate embodiment, a skilled artisan will recognize other combinations, omissions, substitutions and modifications from the disclosure herein. Accordingly, the present invention is not intended to be limited by the reaction of the preferred embodiments, but is to be defined by reference to the appended claims.

What is claimed is:

1. A method of monitoring and displaying patient progress with a rehabilitation protocol, the method comprising:
   automatically measuring at least one parameter of an orthopedic brace used during repetitions of at least one rehabilitation exercise;
   displaying a first indicator representative of a current value of the at least one parameter corresponding to a current repetition; and
   displaying a second indicator representative of a previous maximum attained value of the at least one parameter corresponding to a previous repetition, wherein said first and second indicators are displayed comparatively.

2. The method of claim 1, wherein the previous maximum attained value represents a peak value of the at least one parameter and wherein the method further comprises:
   comparing the current value with the peak value; and
   when the current value exceeds the peak value, storing the current value as the peak value.

3. The method of claim 2 wherein peak value comprises a minimum value and wherein the current value replaces the peak value when the current value is less than the peak value.

4. The method of claim 1, wherein a set comprises a plurality of repetitions of the at least one rehabilitation exercise, and wherein the second indicator represents a peak value of the at least one parameter for the set.

5. The method of claim 1, wherein the at least one parameter comprises one of a torque, an angle, or a range of motion.

6. A method of dynamically normalizing a performance recommendation of a rehabilitation protocol stored in a monitoring device for monitoring at least one parameter of an orthopedic brace used during an exercise, the method comprising:
   indicating a performance recommendation to a patient for a parameter of an exercise of a rehabilitation protocol, wherein the performance recommendation is a percentage of a predetermined amount of effort;
   sensing a value of the parameter from an orthopedic brace during a first performance of the exercise; and
   displaying an indicator corresponding to the value of the parameter as a goal during at least one subsequent performance of the exercise,
     wherein the step of indicating the performance recommendation to the patient includes encouraging the patient to increase his or her performance until a clinician sets the parameter.

7. A method of dynamically normalizing a performance recommendation of a rehabilitation protocol stored in a monitoring device for monitoring at least one parameter of an orthopedic brace used during an exercise, the method comprising:
   indicating a performance recommendation to a patient for a parameter of an exercise of a rehabilitation protocol, wherein the performance recommendation is a percentage of a predetermined amount of effort;
   sensing a value of the parameter from an orthopedic brace during a first performance of the exercise; and
   displaying an indicator corresponding to the value of the parameter as a goal during at least one subsequent performance of the exercise,
     wherein the step of sensing a value includes:
       sensing a current value of the parameter,
       sensing an operator indication that current value corresponds to the percentage of the predetermined amount of effort, and
       storing the current value as the value.

8. A monitoring device for monitoring performance parameters of an exercise routine to determine an operator's compliance-with the exercise routine, the monitoring device comprising:

a memory configured to store recommendations for performance parameters of an exercise routine; and a microcontroller programmed to dynamically normalize at least one recommendation of at least one exercise of the exercise routine to a particular operator through an effort calibration, to use a result of the effort calibration as a goal, and to output a display signal representative of the goal to a display such that the operator attempts to reach the goal during a performance of the at least one exercise.

9. The monitoring device of claim 8, wherein the exercise routine stored in the memory is broken into phases, wherein each phase corresponds to at least one day, and wherein at least one recommendation for the performance parameters of the exercise routine during one of the phases differs from at least one recommendation for another phase.

10. The monitoring device of claim 8, wherein the exercise routine stored in the memory is broken into phases and wherein the microcontroller is further programmed to advance from one phase to another when the operator enters a clinician-provided password or physical key corresponding to phase advancement.

11. The monitoring device of claim 8, wherein the microcontroller is further programmed to output a display signal representative of anatomical graphics showing the operator a recommended performance of one exercise in the exercise routine.

12. The monitoring device of claim 11, wherein the microcontroller is further programmed to output a display signal representative of anatomical graphics showing the operator's performance of the one exercise in the exercise routine such that the operator can visually compare his or her performance to the recommended performance.

13. The monitoring device of claim 11, wherein the anatomical graphics provide pacing for the operator during the performance of the one exercise.

14. A monitoring device for monitoring selected parameters of an orthopedic brace during an exercise routine, the orthopedic brace having a plurality of configurations and visible indicia uniquely identifying at least one of the plurality of configurations of the orthopedic brace, the monitoring device comprising:

a memory configured to store data representing at least one configuration of an orthopedic brace for at least one exercise of an exercise routine, wherein a portion of the data represents values of visual indicia on the orthopedic brace corresponding to the at least one configuration; and a microcontroller programmed to read the data from the memory and output to a display at least the portion of the data representing the values of the visual indicia corresponding to the at least one configuration such that an operator, in preparation of performing the at least one exercise, can set the orthopedic brace to the at least one configuration by using the visual indicia on the orthopedic brace.

15. The monitoring device of claim 14, wherein the visual indicia correspond to designations of angle settings associated with the plurality of configurations of the orthopedic brace.

16. The monitoring device of claim 15, wherein the configurations include one of locks and limits, wherein the locks fix the configuration of the orthopedic brace and the limits fix a range of motion available to the orthopedic brace.

17. The monitoring device of claim 14, wherein the orthopedic brace comprises a knee brace.

18. The monitoring device of claim 14, wherein the exercise routine is broken into phases, wherein each phase corresponds to at least one day, and wherein the value of the visual indicia for the at least one exercise during one of the phases differs from the value of the visual indicia of the at least one exercise during another phase.

19. The monitoring device of claim 14, wherein the exercise routine is broken into phases and wherein the microcontroller is further programmed to advance from one phase to another when an operator enters a clinician-provided password or physical key corresponding to phase advancement.

20. A method of electronically monitoring parameters of an orthopedic brace during performance of an isometric exercise, the method comprising:

monitoring a torque placed on an orthopedic brace during the performance of an exercise;

storing the repetition as a successful repetition when a characteristic of the torque matches a predetermined value, wherein the characteristic of the torque comprises an amount of time that the torque was greater than the predetermined value;

displaying the predetermined value of the torque as a goal on a display;

displaying a current value of the torque on the display such that it may be compared to the goal; and monitoring the amount of time during a repetition of the exercise that the current value is greater than the goal.

21. A method of electronically monitoring parameters of an orthopedic brace during performance of an isometric exercise, the method comprising:

monitoring a torque placed on an orthopedic brace during the performance of an exercise; and storing the repetition as a successful repetition when a characteristic of the torque matches a predetermined value, wherein the exercise is an isometric exercise defined as the leg being at full extension with the orthopedic brace locked at full extension, and as a patient contracts the quadricep muscles.

22. A method of monitoring a performance of an exercise with an electronic device, the method comprising storing data relating to a performance of at least one exercise in a memory of an electronic device, wherein the data does not include information from a torque or range of motion transducer.

* * * * *

UNITED STATES PATENT AND TRADEMARK OFFICE
CERTIFICATE OF CORRECTION

PATENT NO.   : 6,436,058 B1
DATED        : August 20, 2002
INVENTOR(S)  : Krahner et al.

It is certified that error appears in the above-identified patent and that said Letters Patent is hereby corrected as shown below:

Column 28,
Line 51, "used" should be -- using --.

Signed and Sealed this

Third Day of February, 2004

JON W. DUDAS
*Acting Director of the United States Patent and Trademark Office*